United States Patent
Matsubara et al.

(10) Patent No.: US 10,004,750 B2
(45) Date of Patent: Jun. 26, 2018

(54) SALT OF CEPHALOSPORIN DERIVATIVE, ITS CRYSTALLINE SOLID AND A METHOD OF MANUFACTURING THEREOF

(71) Applicant: Shionogi & Co., Ltd., Osaka (JP)

(72) Inventors: Fumihiko Matsubara, Osaka (JP); Takanori Kurita, Hyogo (JP); Daiki Nagamatsu, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days. days.

(21) Appl. No.: 15/508,270

(22) PCT Filed: Sep. 3, 2015

(86) PCT No.: PCT/JP2015/075039
§ 371 (c)(1),
(2) Date: Mar. 2, 2017

(87) PCT Pub. No.: WO2016/035845
PCT Pub. Date: Mar. 10, 2016

(65) Prior Publication Data
US 2017/0281638 A1 Oct. 5, 2017

(30) Foreign Application Priority Data
Sep. 4, 2014 (JP) .................. 2014-179853

(51) Int. Cl.
| A61K 31/546 | (2006.01) |
| A61K 31/185 | (2006.01) |
| C07D 501/16 | (2006.01) |
| C07D 513/04 | (2006.01) |
| C07D 227/06 | (2006.01) |

(52) U.S. Cl.
CPC .......... *A61K 31/546* (2013.01); *A61K 31/185* (2013.01); *C07D 227/06* (2013.01); *C07D 501/16* (2013.01); *C07D 513/04* (2013.01); *A61K 2300/00* (2013.01); *A61K 2800/84* (2013.01)

(58) Field of Classification Search
CPC ...................................... A61K 31/546
USPC ........................................... 544/47
See application file for complete search history.

(56) References Cited

FOREIGN PATENT DOCUMENTS

| EP | 2 341 053 | 6/2011 |
| EP | 2 557 082 | 2/2013 |
| WO | 2014/068388 | 5/2014 |

OTHER PUBLICATIONS

International Search Report and Written Opinion dated Nov. 10, 2015 for Application Serial No. PCT/JP2015/075039, 5 pages.

*Primary Examiner* — Kahsay Habte
(74) *Attorney, Agent, or Firm* — Hamre, Schumann, Mueller & Larson, P.C.

(57) ABSTRACT

The present invention provides an acid addition salt or a sodium salt of a compound represented by the formula (IA):

(IA)

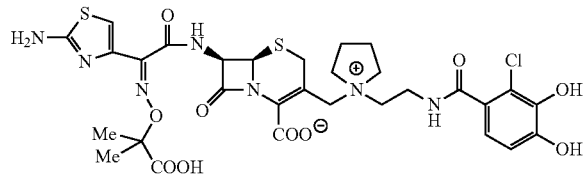

or their hydrate or a stable crystalline solid thereof. The salt or the crystalline solid is extremely useful as an active ingredient for the production of a pharmaceutical product.

28 Claims, 18 Drawing Sheets

[Figure 1]
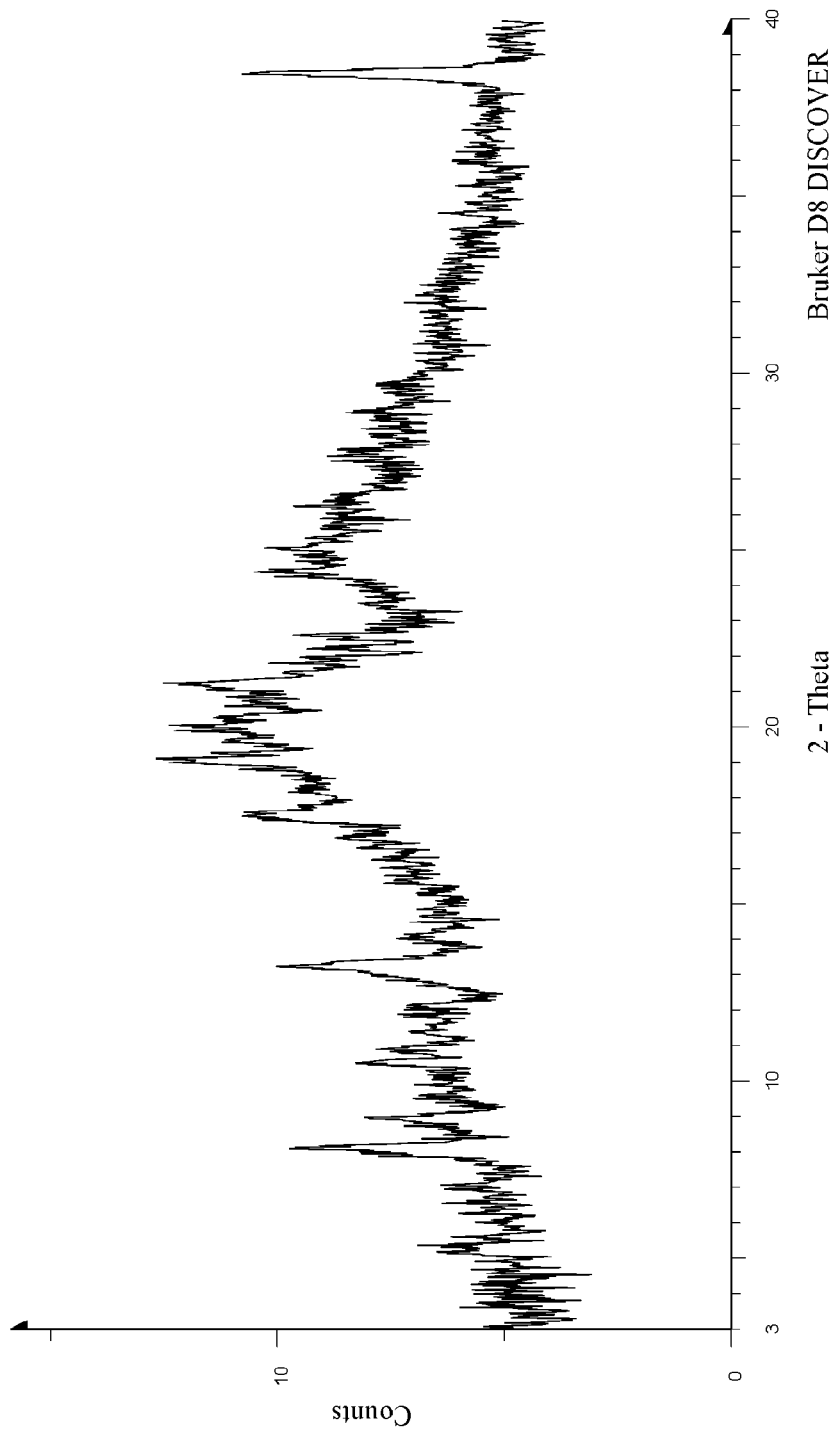

[Figure 2]
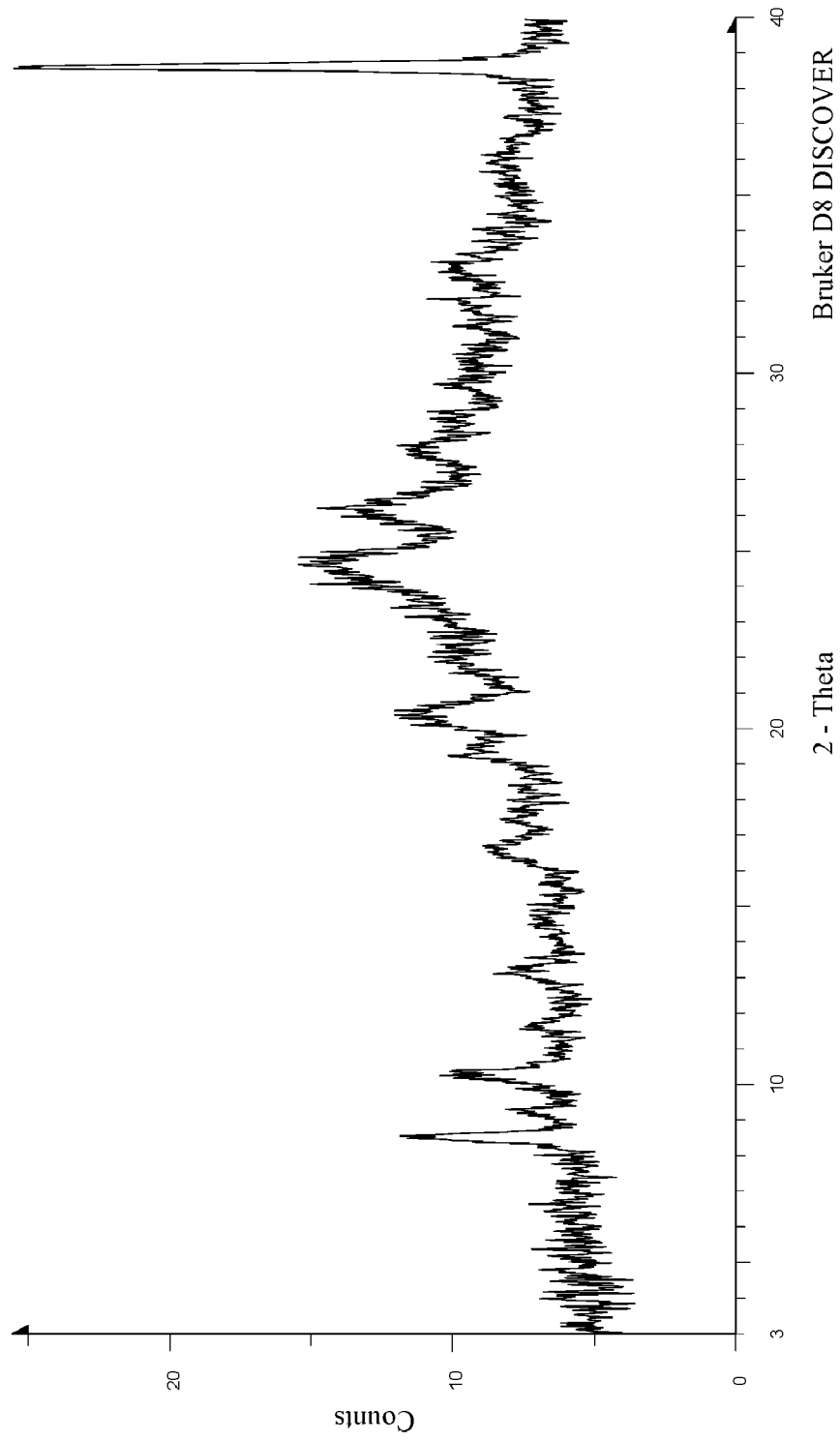

[Figure 3]
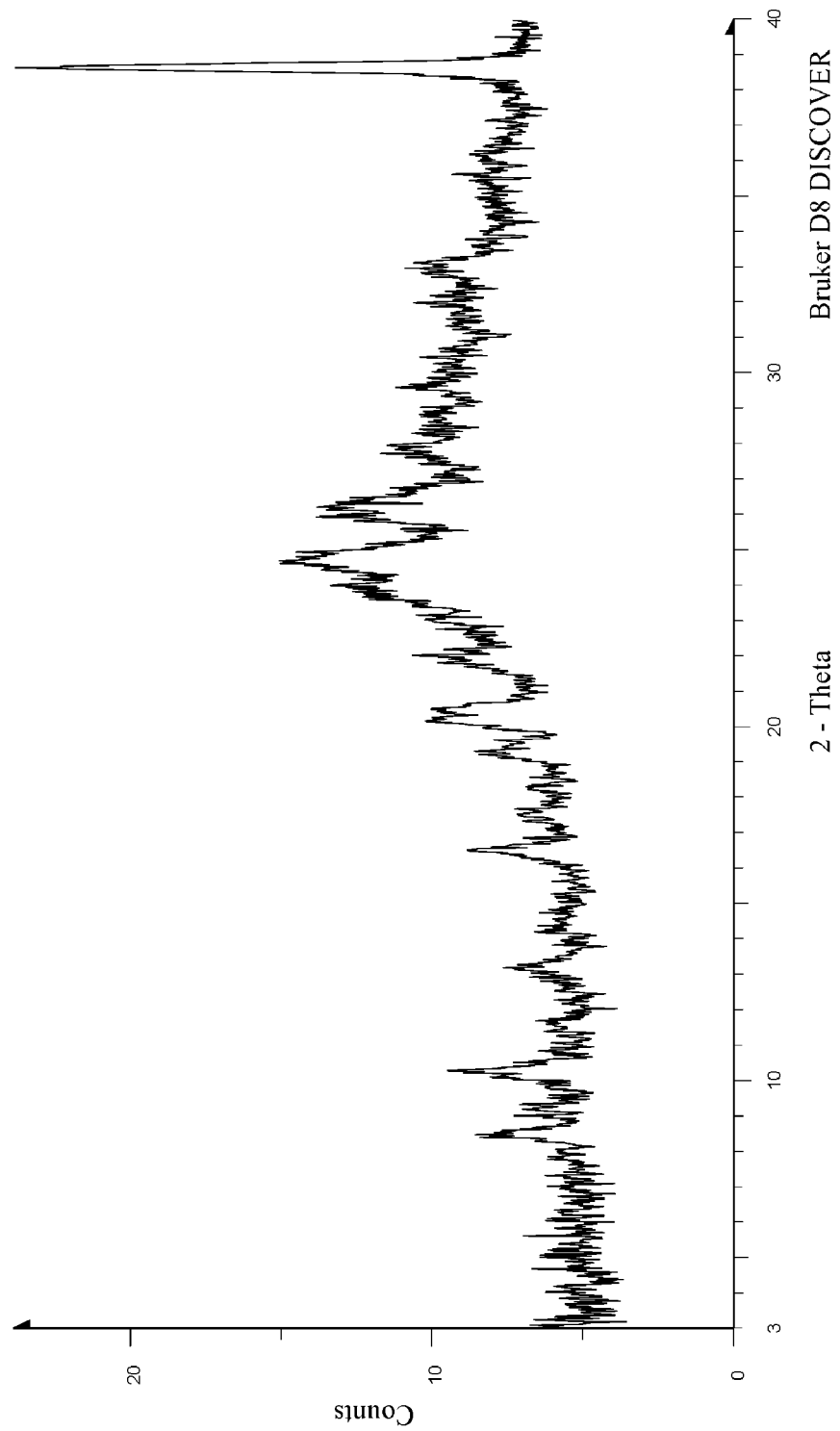

[Figure 4]
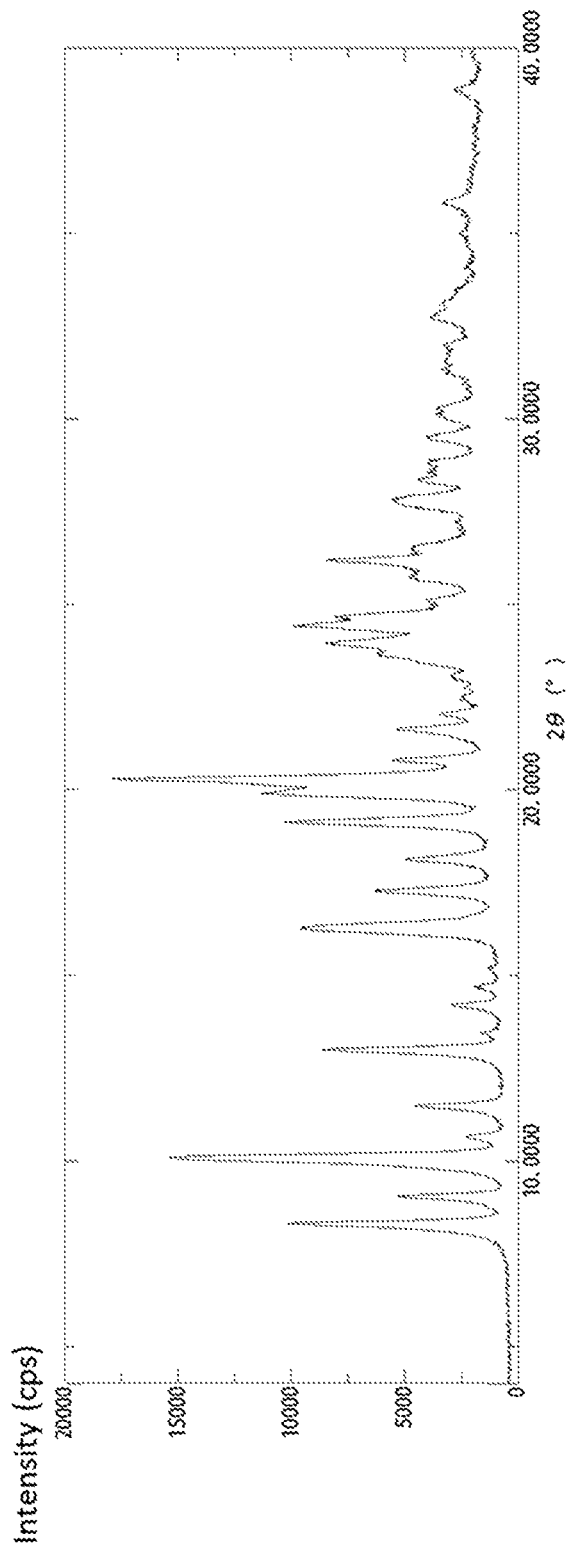

[Figure 5]
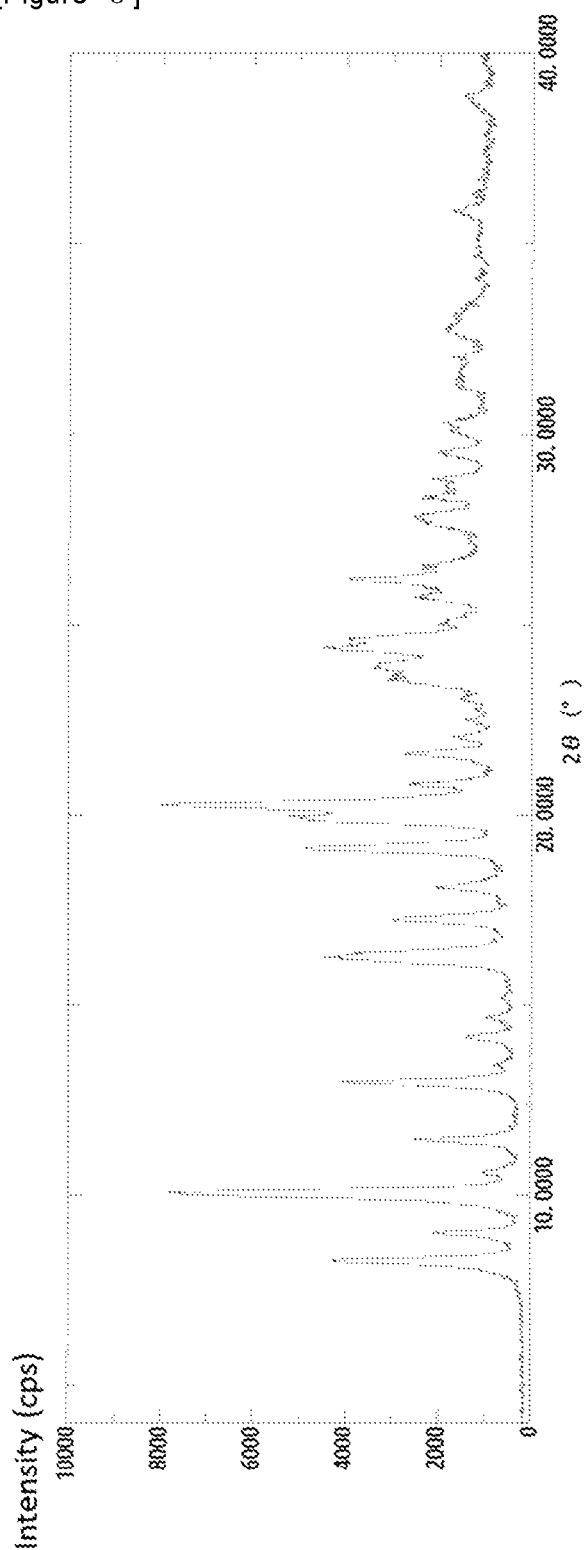

[Figure 6]
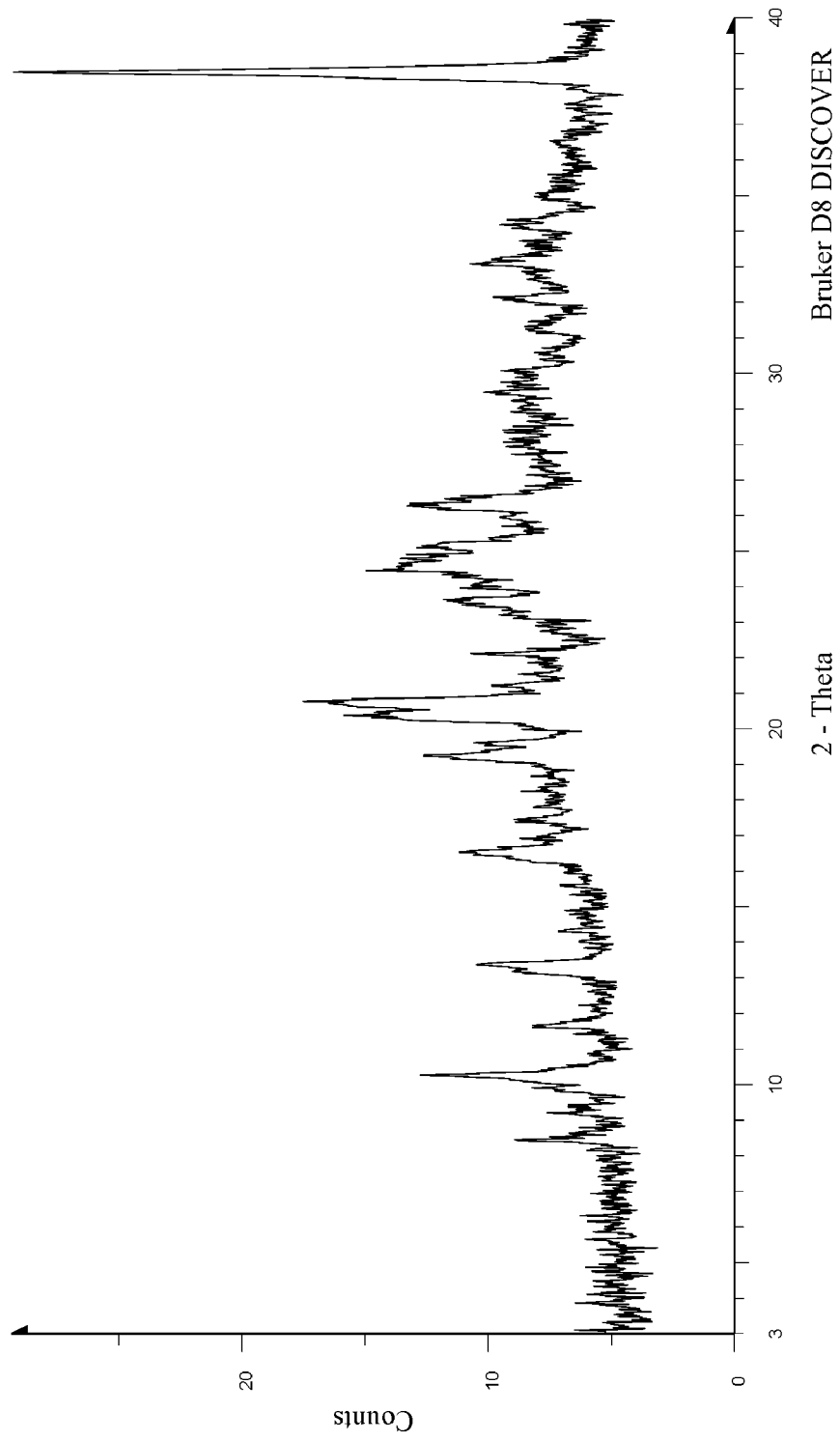

[Figure 7]
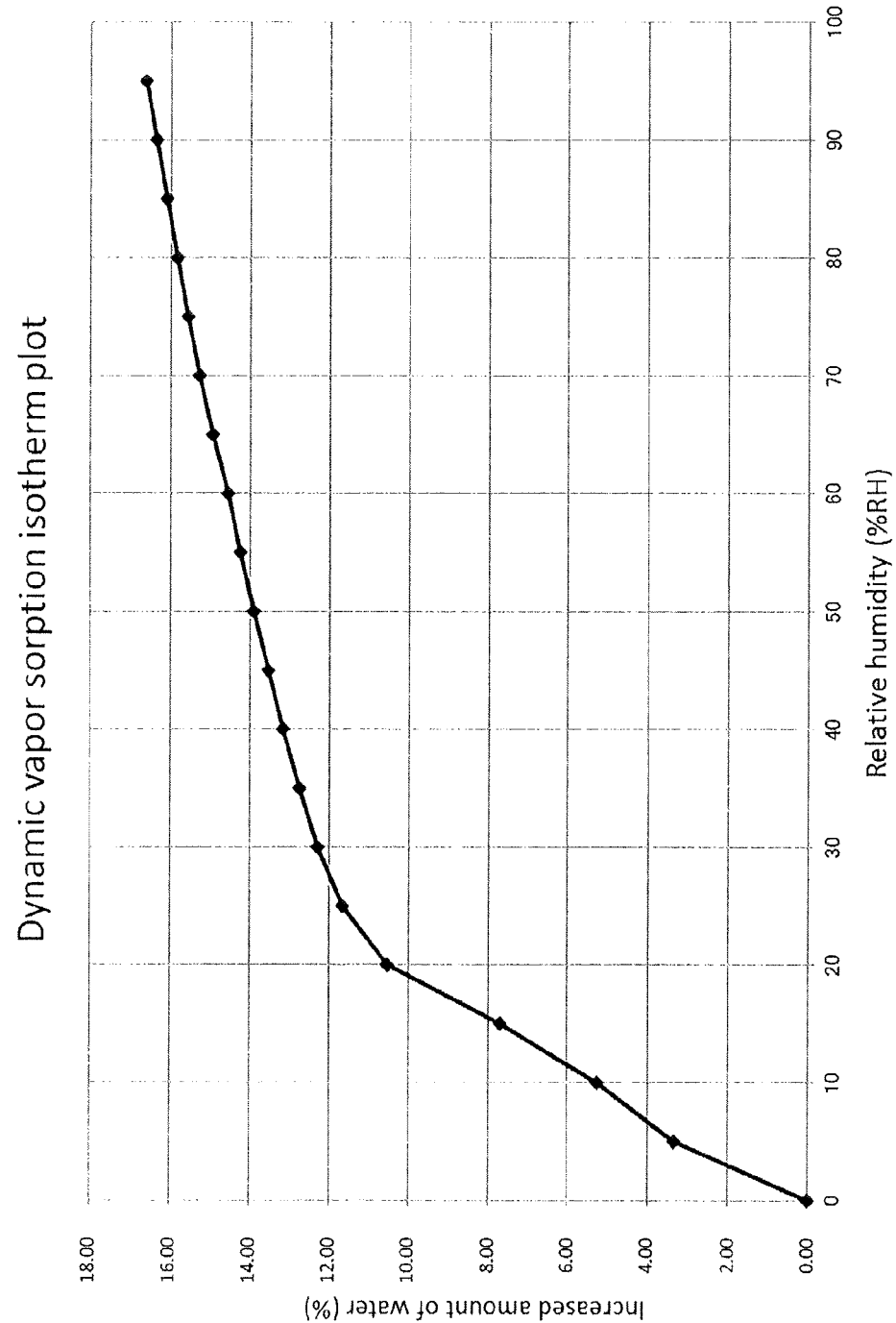

[Figure 8]
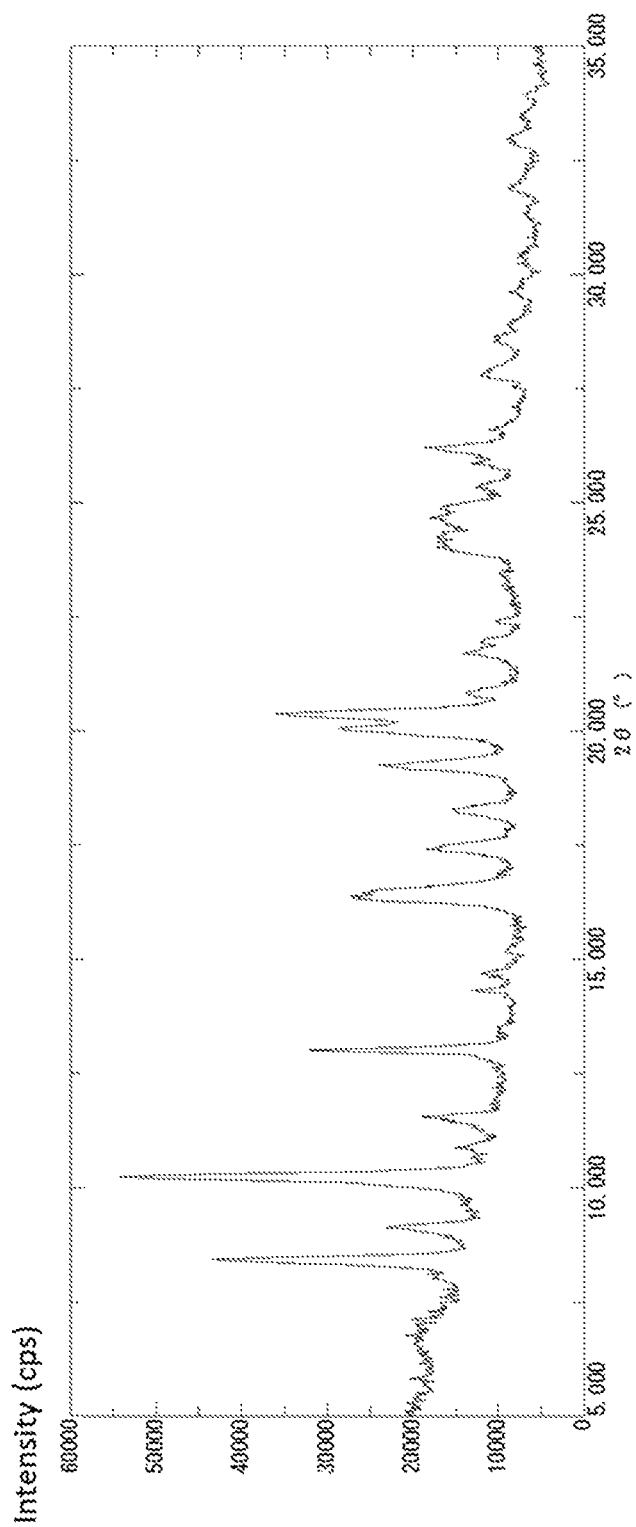

[Figure 9]
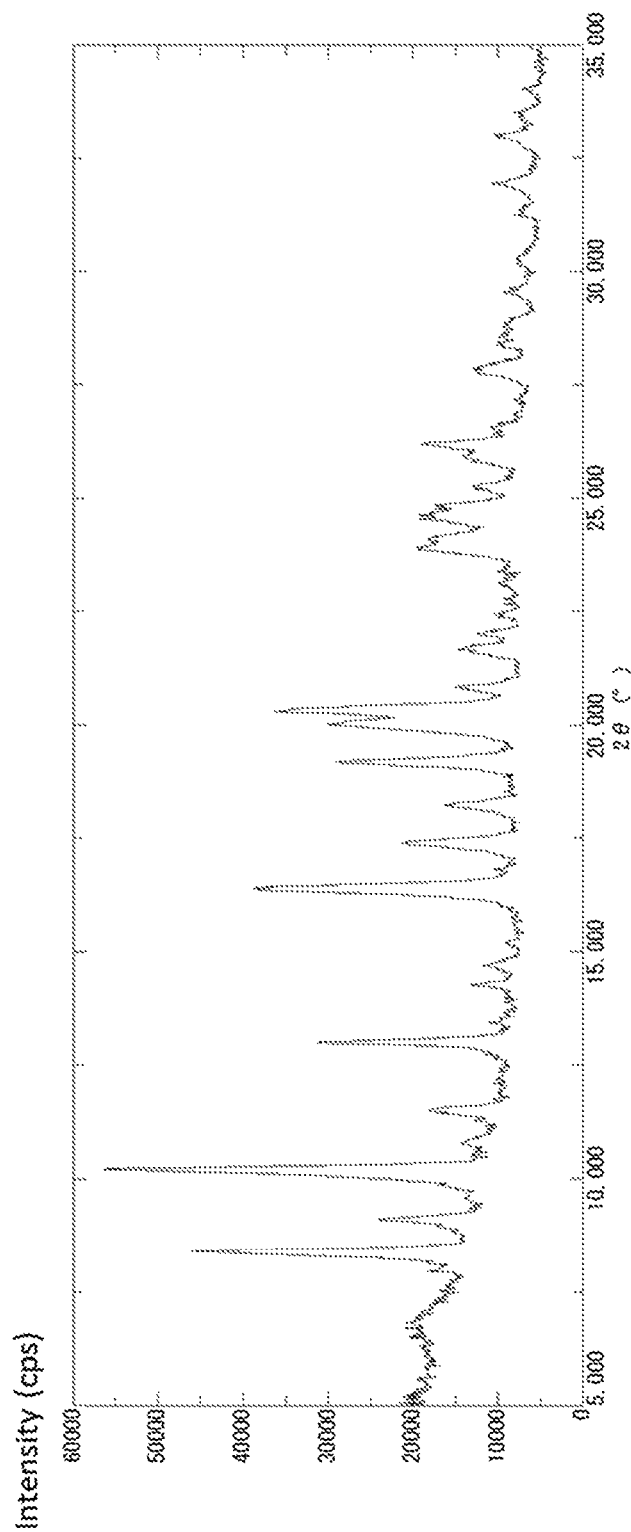

[Figure 10]
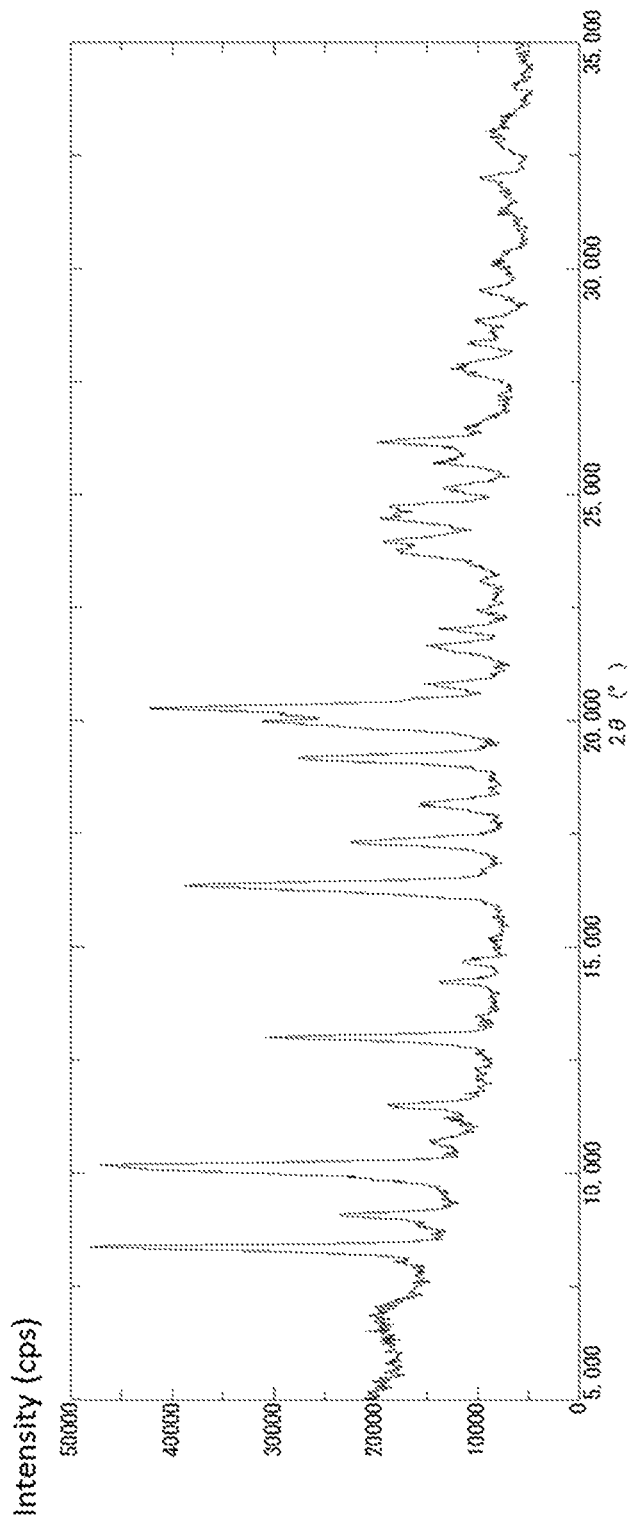

[Figure 1 1]
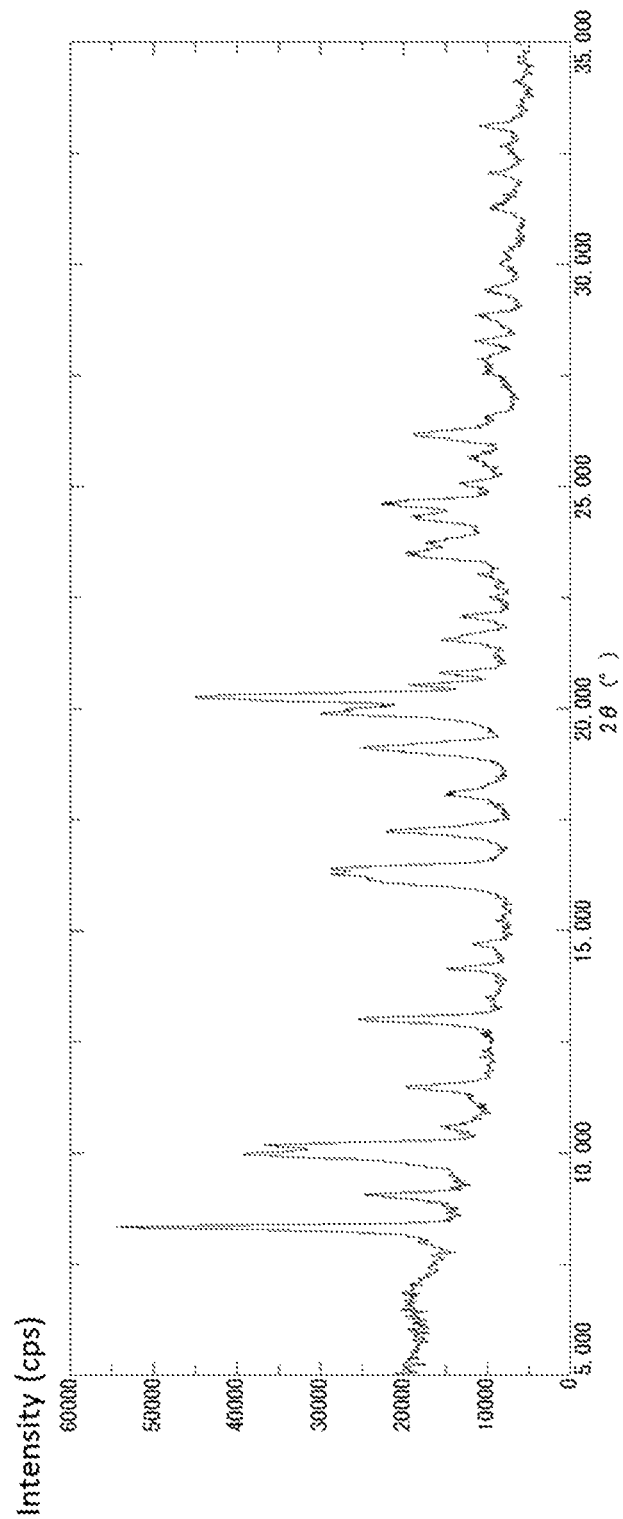

[Figure 1 2]
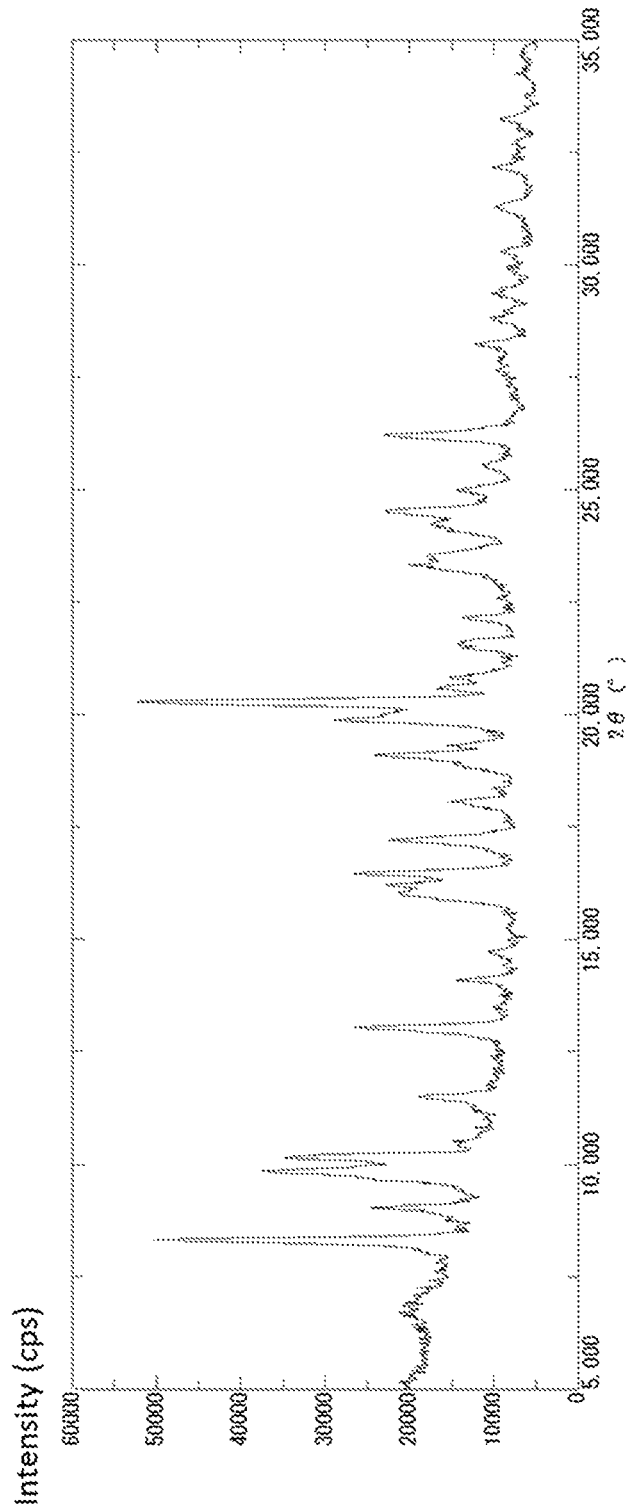

[Figure 13]
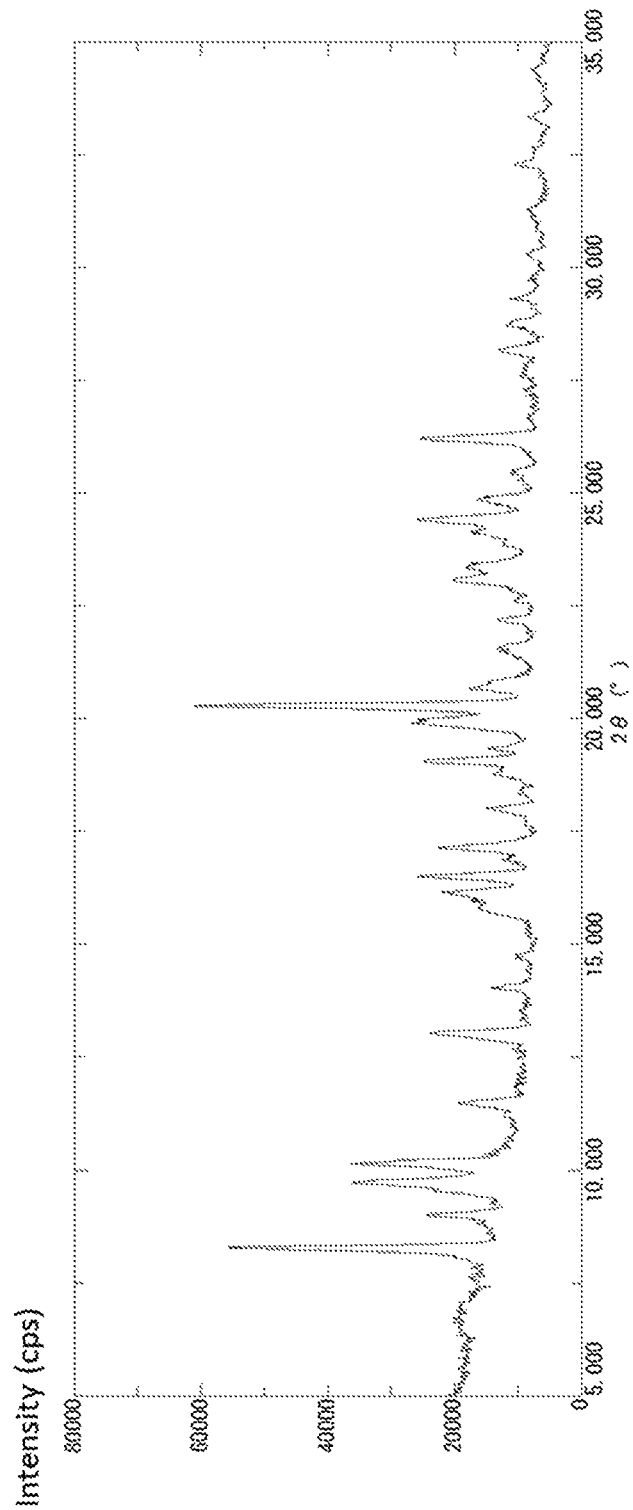

[Figure 1 4]
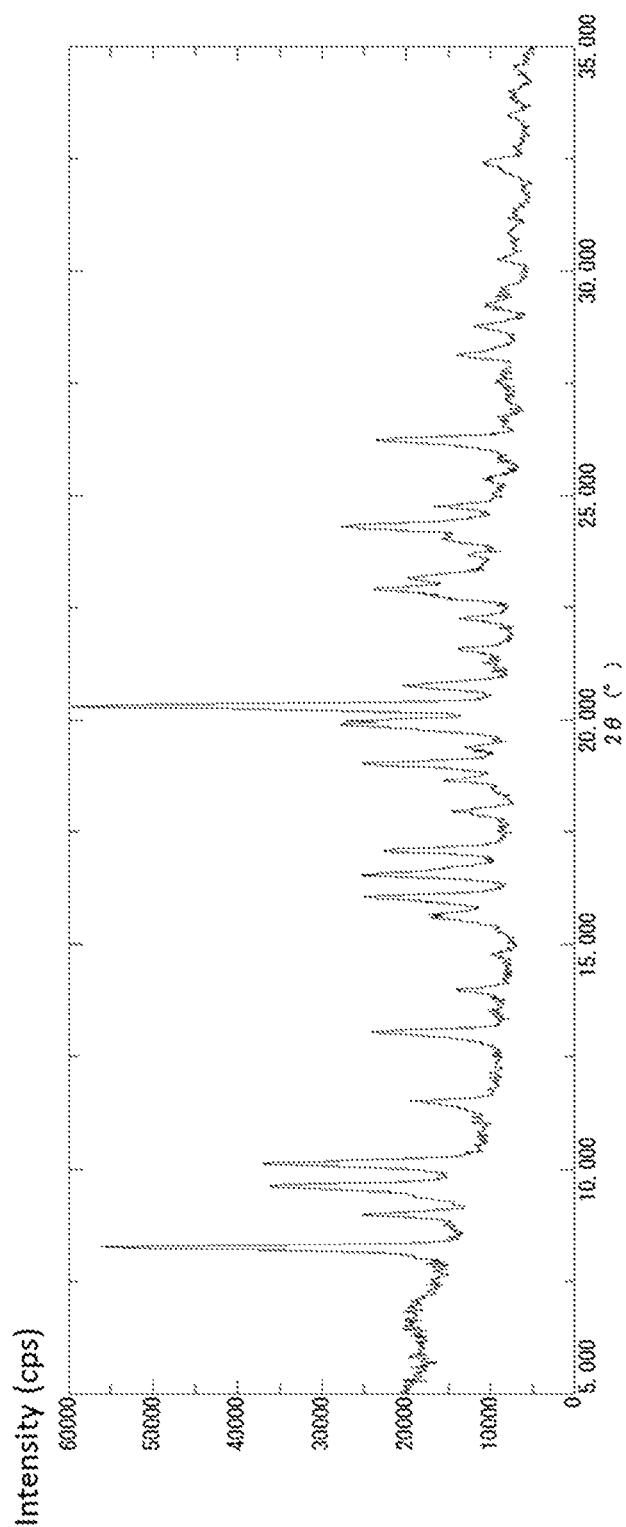

[Figure 1 5]
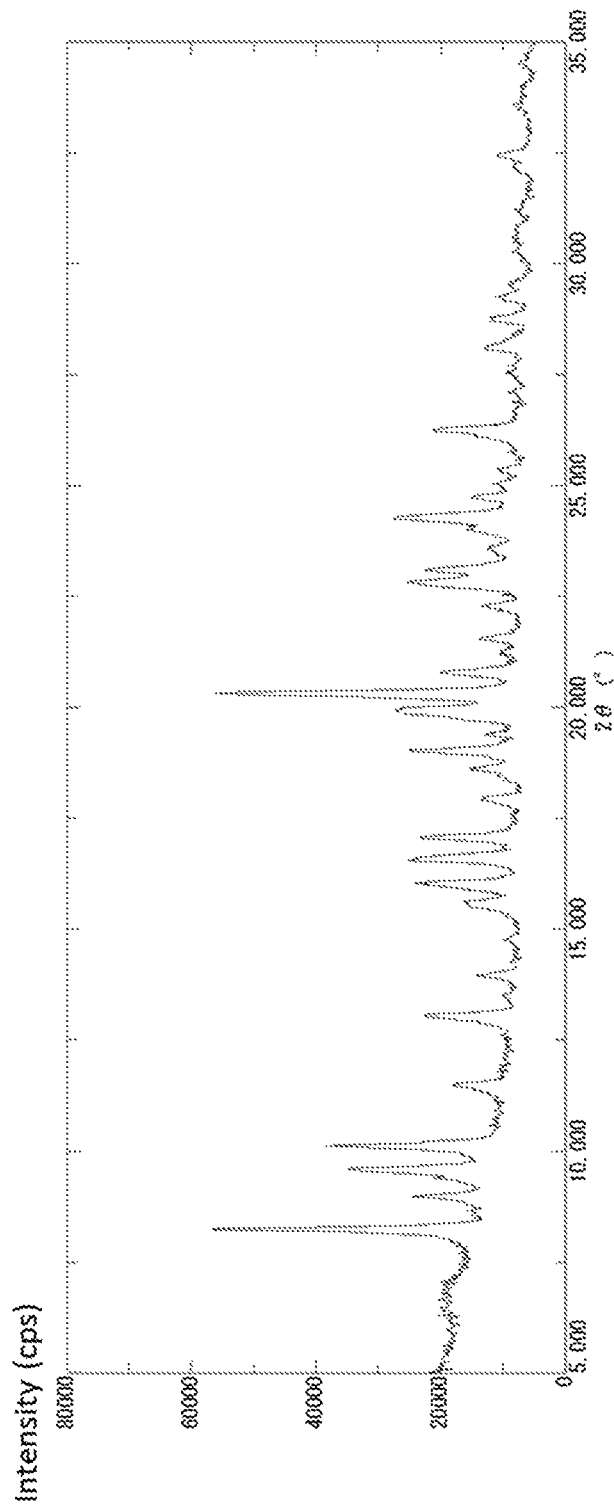

[Figure 16]
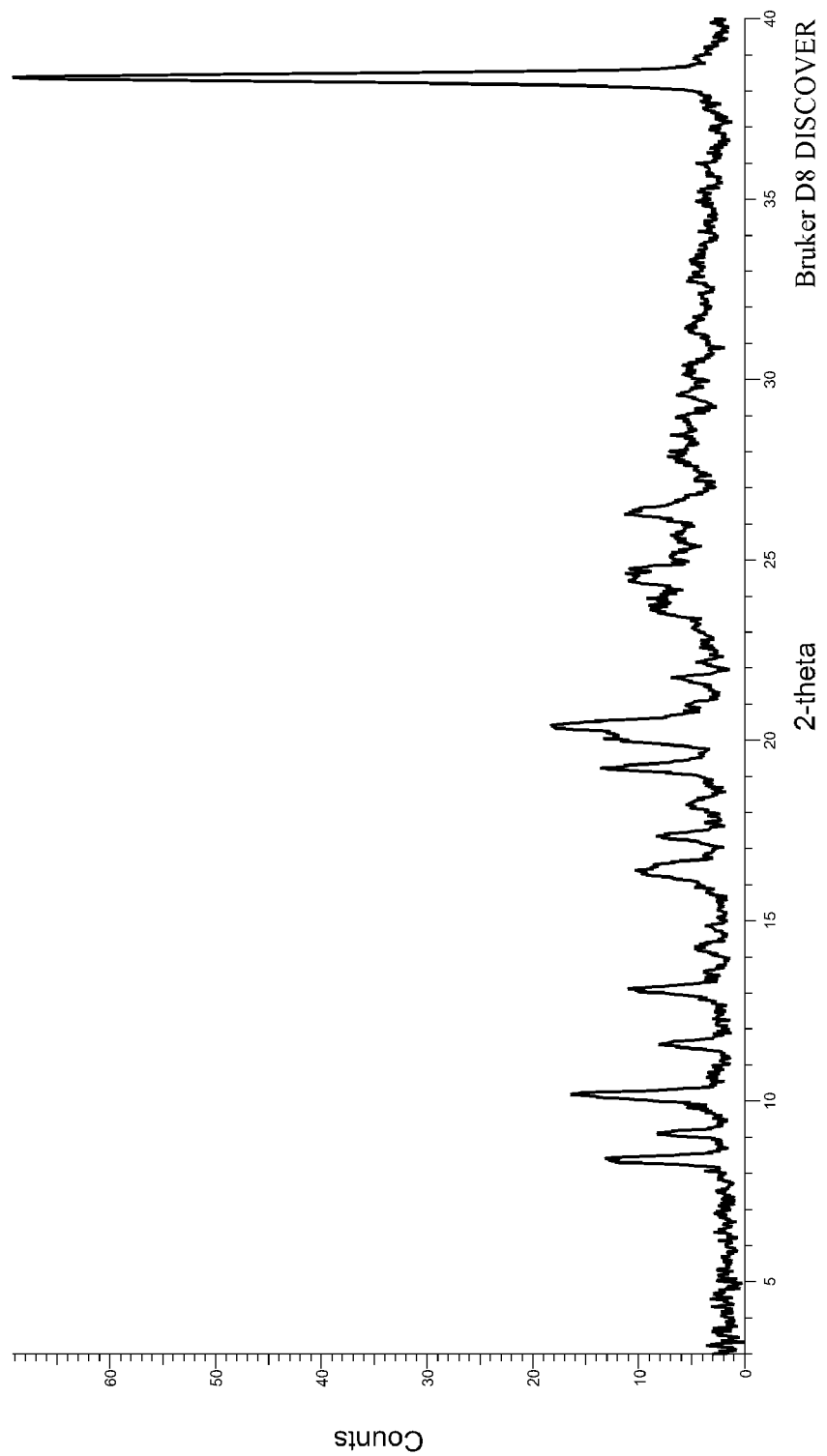

[Figure 17]
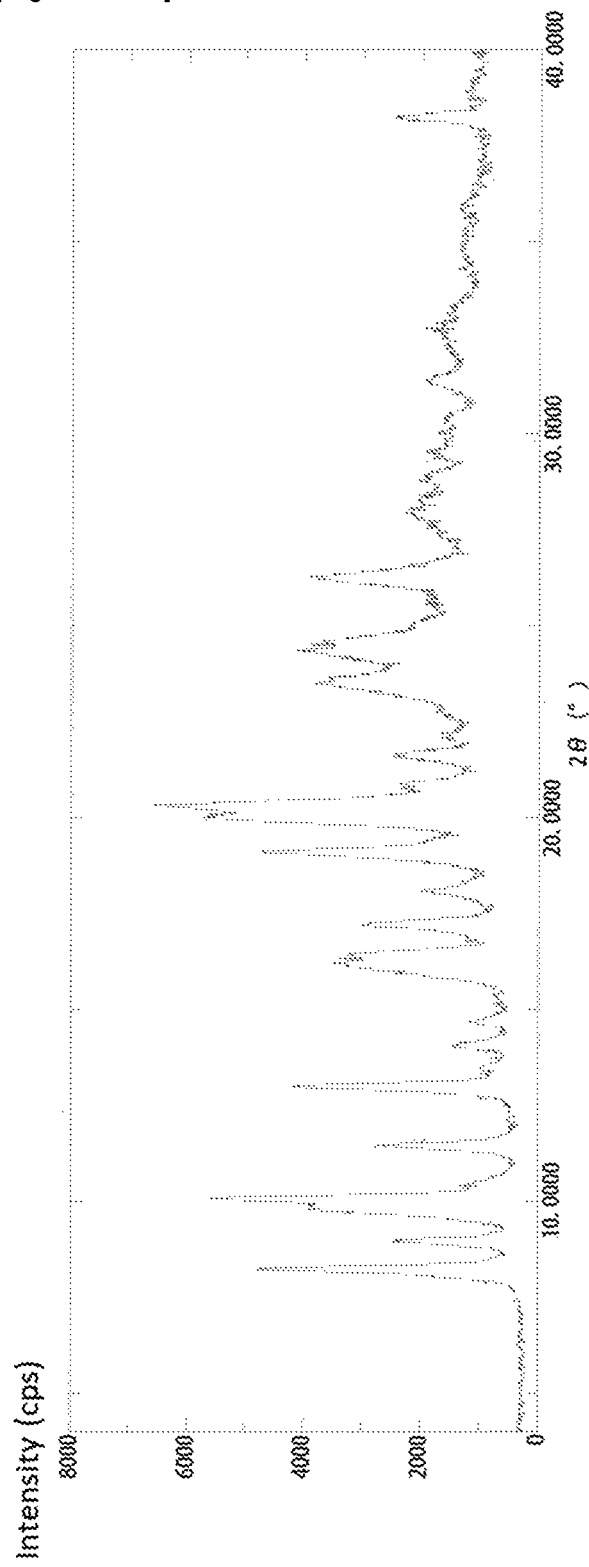

[Figure 18]
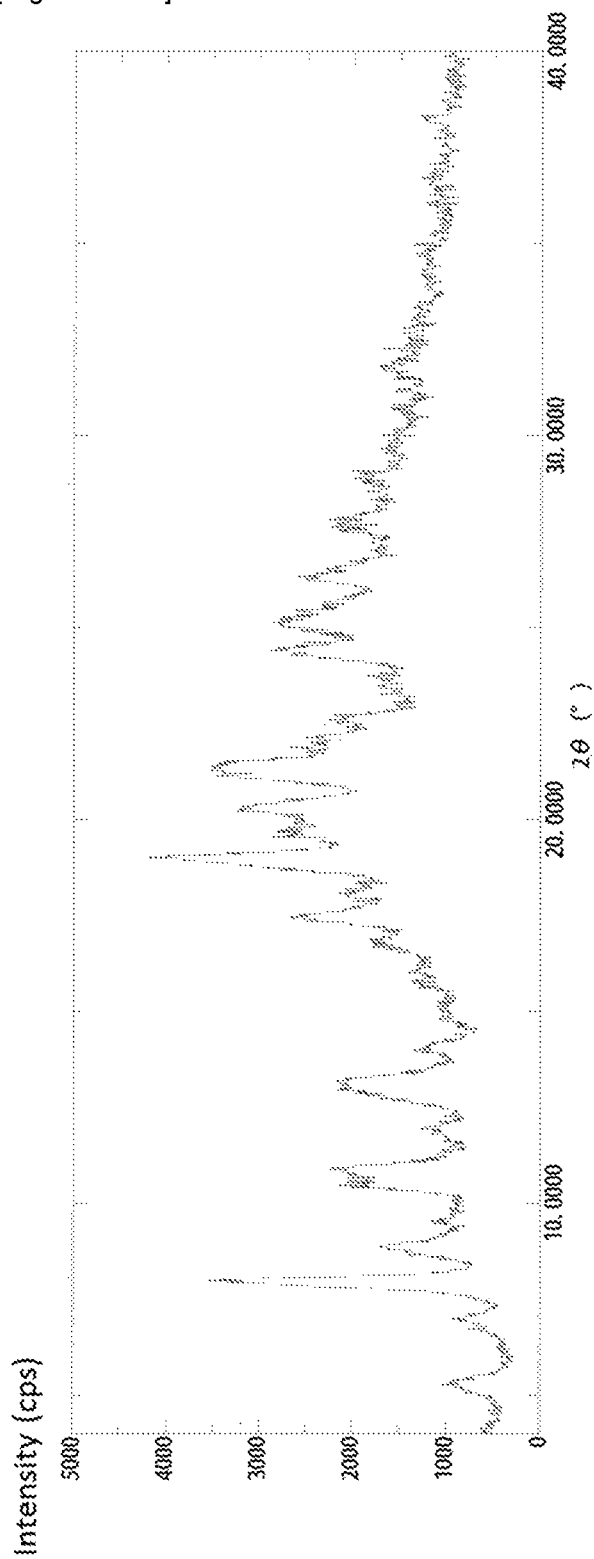

SALT OF CEPHALOSPORIN DERIVATIVE, ITS CRYSTALLINE SOLID AND A METHOD OF MANUFACTURING THEREOF

TECHNICAL FIELD

The present invention relates to a salt of cephalosporin derivative, which is excellent in storage stability, solubility, an operation of formulation or production process, its crystalline solid and a manufacturing method thereof.

BACKGROUND ART

In the manufacturing process of pharmaceuticals, crystalline forms having outstanding chemical or physical properties are desired.

Patent Document 1 by the present applicant describes that a cephalosporin derivative with a catechol group, having broad antibacterial spectrum and a strong antibacterial activity against particular β-lactamase producing bacteria, is useful as a therapeutic or prophylactic agent for infectious diseases. Although the following compound (I-12):

[Chemical formula 1]

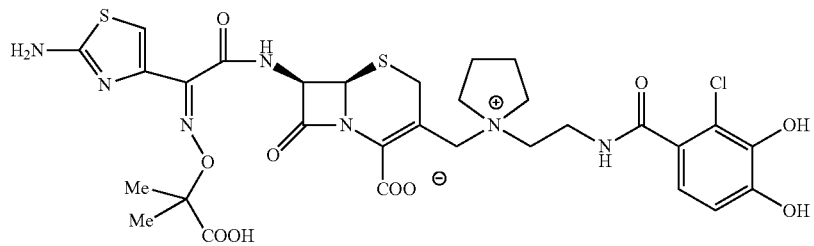

(hereinafter, it is also referred to as a compound (IA)) is disclosed in a form of betaine in Example 12 of the patent document, its sodium salt, its acid addition salt, and solvates thereof are not specifically disclosed. Further, there is no description at all about the crystal thereof.

PRIOR ART DOCUMENTS

Patent Document

[Patent Document 1] International Patent Application Publication WO 2010/050468

SUMMARY OF THE INVENTION

Problems to be Solved by the Invention

A pharmaceutical active ingredient may have substantially different physical properties depending on each solid form. Differences in such physical properties may affect a preparation method or administration method of the pharmaceutical active ingredient or formulation, etc. As one means for improving the physical properties, preparation of salts and crystalline solid are known.

According to study and analysis of the present inventors, the synthesized compound (IA) in Patent Document 1 is an amorphous. Further it was found that using such compound as a pharmaceutically active ingredient or its raw material is not always satisfactory in terms of purity and storage stability, etc. Therefore, the development of a suitable salt or crystalline solid of the compound (IA) is desired.

Although the present inventors tried crystallization of the compound (IA) by using a variety of acids or bases, they were not successful. Especially for acids, they tried crystallization of the acid addition salts of the compound (IA) under more than 1000 conditions using various acids such as hydrochloric acid, sulfuric acid, formic acid, trifluoroacetic acid, phosphoric acid, benzoic acid, methanesulfonic acid etc., while changing the solvent, the temperature, and the crystallization method, but it was found that crystallization thereof is very difficult. Also it was found that solubility of the compound (IA) in water was very low. Therefore, it is recognized that the improvement of the aqueous solubility of the compound (IA) is also required in order to develop the compound (IA) as an injection in particular.

Means for Solving the Problems

As a result of further extensive investigations to solve the above problems, the present inventors have found that the compound (IA) crystallized as stable acid addition salts by using acids having a substituted or unsubstituted benzenesulfonic acid group such as benzenesulfonic acid or p-toluenesulfonic acid. The inventors have further found that the more stable crystals was obtained as a mixed acid addition salt of the compound (IA) by using acid having a substituted or unsubstituted benzenesulfonic acid group together with inorganic acid. Further, the inventors have also found that a sodium salt of the compound (IA) was improved aqueous solubility significantly, and can be used as active ingredient for injection in particular. In addition, the inventors have found to be able to obtain the high purity of sodium salt of the compound (IA) by using acid addition salt thereof.

The present invention provides the followings.

(Item 1) An acid addition salt or a sodium salt of a compound represented by the formula (IA):

[Chemical formula 2]

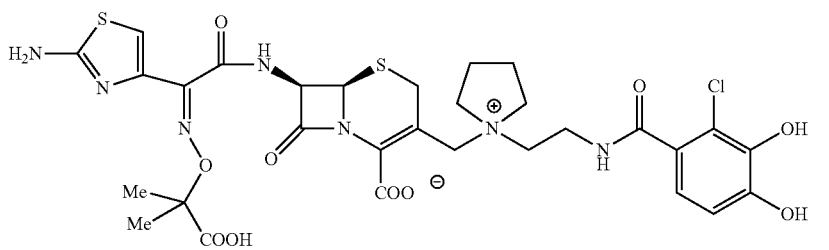

or a hydrate thereof; provided that the acid is 1) an acid having a substituted or unsubstituted benzenesulfonic acid group or 2) a mixed acid comprising an acid having a substituted or unsubstituted benzenesulfonic acid group and an inorganic acid.

(Item 2) The acid addition salt or its hydrate according to Item 1.

(Item 3) The acid addition salt or its hydrate according to Item 1, wherein the salt is formed from acid selected from 1) p-toluenesulfonic acid, 2) benzenesulfonic acid, or 3) a combination p-toluenesulfonic acid or benzenesulfonic acid, and an acid selected from sulfuric acid, hydrochloric acid and hydrobromic acid.

(Item 4) The acid addition salt or its hydrate according to Item 1, wherein the salt is 1) p-toluenesulfonic acid salt, or 3) the salt formed from the combination p-toluenesulfonic acid and sulfuric acid.

(Item 5) The acid addition salt or its hydrate according to Item 4, comprising about 1.0 to about 2.0 mole equivalents of p-toluenesulfonic acid to the compound (IA).

(Item 6) The acid addition salt or its hydrate according to Item 4, comprising about 1.0 to about 1.8 mole equivalents of p-toluenesulfonic acid and about 0.1 to about 0.5 mole equivalents of sulfuric acid to the compound (IA).

(Item 7) The acid addition salt or its hydrate according to any one of Items 1 to 6, which is a crystalline solid.

(Item 8) The acid addition salt or its hydrate according to any one of Items 4 to 6, which is a crystalline solid.

(Item 9) The acid addition salt or its hydrate according to Item 8, which is a single phase crystal or a mixed crystal.

(Item 10) The hydrate according to any one of Items 4 to 9, wherein the content of water is about 12 to 17%.

(Item 11) The mixed crystal according to any one of Items 8 to 10, comprising a single phase crystal of 2 mole equivalents of p-toluenesulfonic acid salt or its hydrate, and a single phase crystal including 1 mole equivalent of p-toluenesulfonic acid salt and 0.5 mole equivalents of sulfuric acid salt or its hydrate.

(Item 11-1) The crystalline solid of the hydrate of the acid addition salt according to any one of Items 7 to 11, comprising 1.3 mole equivalents of p-toluenesulfonic acid and 0.5 mole equivalents of sulfuric acid.

(Item 12) The crystalline solid of the hydrate according to any one of Items 7 to 11, which is a mixed acid addition salt formed from 1.3 mole equivalents of p-toluenesulfonic acid and 0.35 mole equivalents of sulfuric acid.

(Item 13) The crystalline solid of the hydrate of acid addition salt according to any one of Items 7 to 12, comprising about 20.2 to 23.2% of p-toluenesulfonic acid on an anhydrous basis and, about 3.5 to 5.0% of sulfuric acid on an anhydrous basis.

(Item 14) The crystalline solid of the acid addition salt or its hydrate according to any one of Items 8 to 13, wherein the crystalline solid has at least three peaks of diffraction angles (2θ) selected from: 8.2°±0.2°, 10.1°±0.2°, 13.0°±0.2° and 20.3°±0.2° in an X-ray powder diffraction spectrum.

(Item 15) The crystalline solid according to any one of Items 8 to 13, wherein the crystalline solid has at least three peaks of diffraction angles (2θ) selected from: 8.2°±0.2°, 8.9°±0.2°, 10.1°±0.2°, 11.4°±0.2°, 13.0°±0.2°, 19.9°±0.2°, 20.3°±0.2°, 21.5°±0.2° and 26.2°±0.2° in an X-ray powder diffraction spectrum.

(Item 16) The crystalline solid according to any one of Items 8 to 13, wherein the crystalline solid has at least three peaks of diffraction angles (2θ) selected from: 8.2°±0.2°, 8.9°±0.2°, 10.1°±0.2°, 13.0°±0.2°, 16.5°±0.2°, 17.1°±0.2°, 17.9°±0.2°, 19.0°±0.2°, 20.3°±0.2° and 26.2°±0.2° in an X-ray powder diffraction spectrum.

(Item 17) A pharmaceutical composition comprising the acid addition salt, its hydrate or the crystalline solid thereof according to any one of Items 1 to 16.

(Item 18) A process for preparing the crystalline solid of the acid addition salt or its hydrate according to any one of Items 8 to 16, characterized by adding p-toluenesulfonic acid and sulfuric acid to a solution containing the compound (IA).

(Item 19) The process for preparing the crystalline solid according to Item 18, characterized by adding about 2.2 to 2.5 wt % of p-toluenesulfonic acid monohydrate and about 5 to 6 wt % of 75% sulfuric acid to the column eluate containing the compound (IA).

(Item 20) A sodium salt or its hydrate according to Item 1.

(Item 21) The sodium salt or its hydrate according to Item 20, which is an amorphous.

(Item 22) A pharmaceutical composition comprising the sodium salt or its hydrate according to Item 20 or 21.

(Item 23) The pharmaceutical composition according to Item 22, which is a lyophilized formulation.

(Item 24) A method for preparing a lyophilized formulation comprising a sodium salt of the compound (IA) or its hydrate, characterized by using the acid addition salt, its hydrate or the crystalline solid thereof according to any one of Items 1 to 16.

(Item 25) A method for preparing a lyophilized formulation comprising a sodium salt of the compound (IA) or its hydrate, characterized by freeze-drying a solution containing the acid addition salt, its hydrate or the crystalline solid thereof according to any one of Items 1 to 16 and sodium hydrate.

(Item 26) The method for preparing an acid addition salt according to Item 24 or 25, wherein the acid addition salt is formed from 1) p-toluenesulfonic acid, or 3) combination of p-toluenesulfonic acid and sulfuric acid.

(Item 27) A pharmaceutical composition containing the compound (IA), its pharmaceutically acceptable salt or a hydrate thereof, and further sodium p-toluenesulfonate and/or sodium sulfate.

(Item 28) The pharmaceutical composition according to Item 27, containing a sodium salt of the compound (IA) or its hydrate, and further sodium p-toluenesulfonate and/or sodium sulfate.

(Item 29) A pharmaceutical composition comprising a sodium salt or an acid addition salt of the compound (IA), its solvate, or a crystalline solid thereof according to Item 1, for parenteral administration.

(Item 30) The pharmaceutical composition according to Item 29, for dermal, subcutaneous, intravenous, intraarterial, intramuscular, intraperitoneal, transmucosal, inhalation, transnasal, ophthalmic, inner ear, or vaginal administration.

(Item 31) The pharmaceutical composition according to any one of Items 29 to 31, which is injection, infusion, eye drop, nose drop, ear drop, aerosol, inhalation, lotion, impregnation, liniment, mouthwash, enema, ointment, plaster, jelly, cream, patch, cataplasm, external powder or suppository.

(Item 32) A pharmaceutical composition comprising a sodium salt or an acid addition salt of the compound (IA) or their solvate, or a crystalline solid thereof according to Item 1, for pediatric or geriatric patient.

Effects of the Invention

The present invention provides an acid addition salt or a sodium salt of the compound (IA), or a solvate thereof. In particular, the acid addition salt is preferably provided that as a crystalline solid.
The salts, its salvates or the crystalline solid thereof has at least one of the following features:
(1) good stability to heat, humidity, solvates, light etc., high storage stability.
(2) good stability to coloration.
(3) good solubility in water or organic solvent.
(4) a fast dissolution rate in water or organic solvent.
(5) high purity.
(6) low residual ratio of organic solvent.
(7) excellent operation for filtration, centrifugation, formulation etc.
(8) small specific volume.
(9) it is difficult to charge.
(10) it is possible to be produced in high yield under low environmental impact and be manufactured in volume.
(11) it is useful as a pharmaceutical active ingredient for an injection or a source material for manufacturing them.
(12) it is possible to be adjusted in proper pH to inject into a vein without vascular pain, therefore it has an advantage in control of fluid volume or reduction excipients at the time of formulation.
In particular, a crystalline solid of the present invention has high stability under the condition of the wide humidity range (e.g.: 25 to 99% RH) or even in harsh environment (e.g.: high humidity).

BRIEF EXPLANATION OF THE DRAWINGS

Hereinafter, the type I crystal means a crystalline solid of the hydrate of the mixed acid salt of the compound (IA), wherein the mixed acid salt is formed from 1.3 mole equivalents of p-toluenesulfonic acid and 0.35 mole equivalents of sulfuric acid.
FIG. 1 shows an X-ray powder diffraction spectrum of the crystalline solid of 8.5 hydrates of 2 mole equivalents p-toluenesulfonic acid salt of the compound (IA) obtained in Example 3. The horizontal axis represents a diffraction angle 2θ(°), the vertical axis represents intensity (Count).

FIG. 2 shows an X-ray powder diffraction spectrum of the crystalline solid of the mixed acid salt of the compound (IA) obtained in Example 4, wherein the mixed acid salt is formed from 1 mole equivalent of p-toluenesulfonic acid and 1 mole equivalent of hydrochloric acid.

FIG. 3 shows an X-ray powder diffraction spectrum of the crystalline solid of the mixed acid salt of the compound (IA) obtained in Example 5, wherein the mixed acid salt is formed from 1 mole equivalent of p-toluenesulfonic acid and 1 mole equivalent of hydrobromic acid.

FIG. 4 shows an X-ray powder diffraction spectrum of the type I crystal D obtained in Example 6-1, wherein water content is 13.5%±0.3%.

FIG. 5 shows an X-ray powder diffraction spectrum of the type I crystal E obtained in Example 6-2, wherein water content is 13.8%±0.3%.

FIG. 6 shows an X-ray powder diffraction spectrum of the crystalline solid of 2 mole equivalents of bensenesulfonic acid salt of the compound (IA) obtained in Example 7.

FIG. 7 shows a dynamic vapor sorption isotherm plot of the type I crystal D conducted in Example 8.

FIG. 8 shows an X-ray powder diffraction spectrum of the type I crystal D, which was measured under the condition of 30% RH in Example 8.

FIG. 9 shows an X-ray powder diffraction spectrum of the type I crystal D, which was measured under the condition of 40% RH in Example 8.

FIG. 10 shows an X-ray powder diffraction spectrum of the type I crystal D, which was measured under the condition of 50% RH in Example 8.

FIG. 11 shows an X-ray powder diffraction spectrum of the type I crystal D, which was measured under the condition of 60% RH in Example 8.

FIG. 12 shows an X-ray powder diffraction spectrum of the type I crystal D, which was measured under the condition of 70% RH in Example 8.

FIG. 13 shows an X-ray powder diffraction spectrum of the type I crystal D, which was measured under the condition of 80% RH in Example 8.

FIG. 14 shows an X-ray powder diffraction spectrum of the type I crystal D, which was measured under the condition of 90% RH in Example 8.

FIG. 15 shows an X-ray powder diffraction spectrum of the type I crystal D, which was measured under the condition of 95% RH in Example 8.

FIG. 16 shows an X-ray powder diffraction spectrum of the crystalline solid of the hydrate of the mixed acid salt of the compound (IA) obtained in Example 11, wherein the mixed acid salt is formed from 1.05 mole equivalents of p-toluenesulfonic acid and 0.65 mole equivalents of sulfuric acid.

FIG. 17 shows an X-ray powder diffraction spectrum of the crystalline solid of the hydrate of the mixed acid salt of the compound (IA) obtained in Example 12, wherein the mixed acid salt is formed from 1.0 mole equivalent of p-toluenesulfonic acid and 0.5 mole equivalents of sulfuric acid.

FIG. 18 shows an X-ray powder diffraction spectrum of the crystalline solid of the hydrate of 2.0 mole equivalent of p-toluenesulfonic acid salt of the compound (IA).

MODE FOR CARRYING OUT THE INVENTION

Herein, although the compound (IA) is represented by the formula (IA):

[Chemical formula 3]

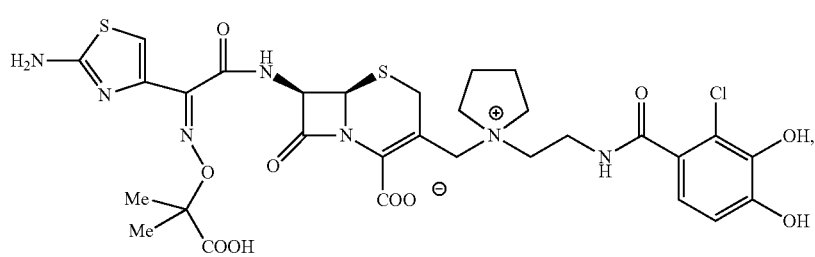

(IA)

it can substantially go into the state of the formula (IA'):

[Chemical formula 4]

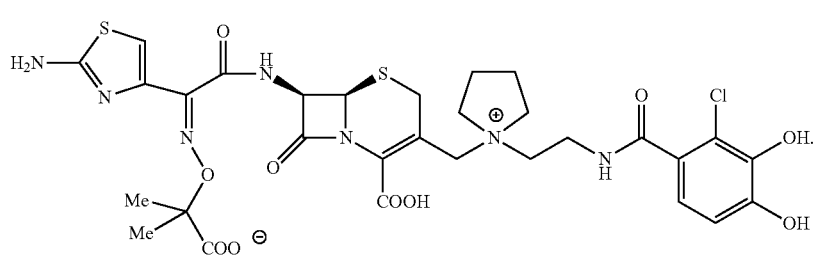

(IA')

Therefore, the compound (IA) includes both structures. For example, the sodium salt of the compound (IA) includes,

[Chemical formula 5]

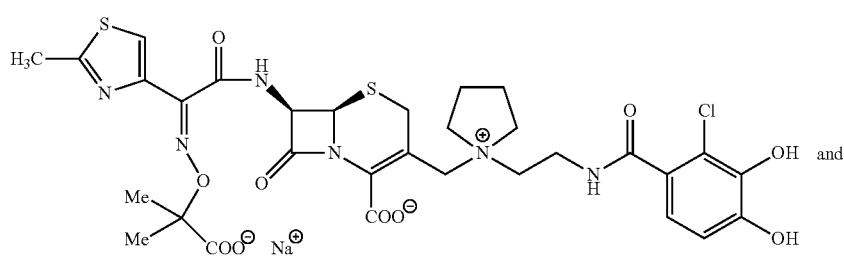

and

[Chemical formula 6]

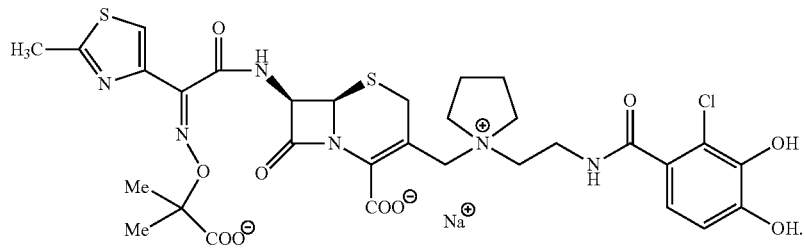

Salt formation studies provide a means of altering the phydicochemical and resultant biological characteristics of a drug without modifying its chemical structure. A salt form can have a dramatic influence on the properties of the drug. The selection of a suitable salt is partially dictated by yield, rate and quantity of the crystalline structure. In addition, hygroscopicity, stability, solubility and the process profile of the salt form are important considerations. Solubility of a salt form can affect its suitability for use as a drug. Where aqueous solubility is low, i.e. less than 10 mg/ml, the dissolution rate at in vivo administration can be rate limiting in the absorption process leading to poor bioavailability. Moreover, low solubility in water can be limited choice of suitable administration routes since it is difficult for administration by injection.

An acid to be used for forming an acid addition salts of the compound (IA) includes one or two acids selected from acids having a substituted or unsubstituted benzenesulfonic acid group and inorganic acids (e.g.: sulfuric acid, hydrochloric acid, nitric acid, hydrobromic acid, phosphoric acid, boric acid, etc.). In particular, the acid having a substituted or unsubstituted benzenesulfonic acid group is preferably p-toluenesulfonic acid, benzenesulfonic acid, trifluoromethyl benzenesulfonic acid, chlorobenzenesulfonic acid, methoxybenzenesulfonic acid or the like, more preferably benzenesulfonic acid, p-toluenesulfonic acid or the like. The inorganic acid is more preferably hydrochloric acid, sulfuric acid or the like. Moreover the acid addition salt may be selected from a mixed acid salt which is formed from a combination of two or more acids selected from these acids, so a mixed acid salt is preferably formed from a combination of an acid having a substituted or unsubstituted benzenesulfonic acid group and an inorganic acid. Particularly the mixed acid salt formed from p-toluenesulfonic acid and hydrochloric acid, or the mixed acid salt formed from p-toluenesulfonic acid sulfuric acid has high stability to humidity etc. and excellent storage stability. Although the acid addition salt is preferably crystalline solid, it may be a single phase crystal or a mixed crystal.

A single phase crystal may be formed from a single kind of acid addition salt or a mixed acid salt of two or more kinds of acid. A mixed crystal is a crystalline solid, wherein two or more kinds of single phase crystals are present as a mixture. For example, a mixed crystal may be a mixture of a crystalline solid of an acid addition salt, wherein the acid is an acid having substituted or unsubstituted benzenesulfonic acid group, and a crystalline solid of a mixed acid addition salt formed from a combination of an acid having substituted or unsubstituted benzenesulfonic acid group and an inorganic acid, or also be a mixture of a crystalline solid of a mixed acid addition salt formed form a combination of an acid having substituted or unsubstituted benzenesulfonic acid group and an inorganic acid and the other crystalline solid of a mixed acid salt formed from a combination of an acid having substituted or unsubstituted benzenesulfonic acid group and an inorganic acid, which is different from the above combination.

The amount range of a mixed acid of an acid having substituted or unsubstituted benzenesulfonic acid group and inorganic acid to the compound (IA) is preferably an arbitrary combination of about 1.0 to 1.9 mole equivalents of an acid having a substituted or unsubstituted benzenesulfonic acid group and about 0.1 to 0.9 mole equivalents of an inorganic acid, more preferably an arbitrary combination of about 1.0 to 1.5 mole equivalents of an acid having substituted or unsubstituted benzenesulfonic acid group and about 0.2 to 0.7 mole equivalents of an inorganic acid. Further preferred amount range thereof is an arbitrary combination of about 1.2 to 1.4 mole equivalents of an acid having substituted or unsubstituted benzenesulfonic acid group and about 0.3 to 0.7 mole equivalents of an inorganic acid. The number of mole equivalents of the acid may contain an acid as a residual solvent such as adhered acid.

As embodiments of an acid addition salt of the present invention or its solvate, preferably a crystalline solid, p-toluenesulfonic acid salt (non-solvete) of the compound (IA), hydrate of p-toluenesulfonic acid salt, a mixed acid salt formed from p-toluenesulfonic acid and sulfuric acid (hereinafter, p-toluenesulfonic acid-sulfuric acid mixed acid salt) (non-solvate), hydrate of p-toluenesulfonic acid-sulfuric acid salt, a mixed acid salt formed from p-toluenesulfonic acid and hydrochloric acid (hereinafter, p-toluenesulfonic acid-hydrochloric acid mixed acid salt)(non-solvate), hydrate of p-toluenesulfonic acid-hydrochloric acid mixed acid salt, a mixed acid salt formed from p-toluenesulfonic acid and hydrobromic acid (hereinafter, p-toluenesulfonic acid-hydrobromic acid mixed acid salt) (non-solvate), hydrate of p-toluenesulfonic acid-hydrobromic acid mixed acid salt, a mixed acid salt formed from p-toluenesulfonic acid and nitric acid (hereinafter, p-toluenesulfonic acid and nitric acid mixed acid salt) (non-solvate), hydrate of p-toluenesulfonic acid-nitric acid mixed acid salt, a salt formed from benzenesulfonic acid (non-solvate), hydrate of a salt formed from benzenesulfonic acid and the like can be exemplified.

The kinds and content of the acid contained in the acid addition salt of the present invention, its solvate, or crystalline solid thereof includes, relative to the compound (IA), 1) about 1 to 2 mole equivalent of p-toluenesulfonic acid, 2) a mixed acid comprising about 1.0 to 1.9 mole equivalents of p-toluenesulfonic acid and about 0.1 to 0.9 mole equivalents of sulfuric acid, 3) a mixed acid comprising about 1.0 to 1.9 mole equivalent of p-toluenesulfonic acid and about 0.1 to 1.0 mole equivalents of hydrochloric acid, 4) a mixed acid comprising about 1.0 to 1.9 mole equivalents of p-toluenesulfonic acid and about 0.1 to 1.0 mole equivalents of hydrobromic acid, 5) a mixed acid comprising about 1.0 to 1.9 mole equivalents of p-toluenesulfonic acid and about 0.1 to 1.0 mole equivalents of nitric acid, and 6) about 1 to 2 mole equivalents of benzenesulfonic acid and the like. The number of mole equivalents of the acid may contain an acid as a residual solvent such as adhered acid, the number of mole equivalents of the salvate may contain a residual solvent such as adhered solvent.

In particular, a preferred embodiment of a crystalline solid of non-solvate or solvent of a mixed acid salt of the compound (IA), wherein the mixed acid is formed from about 1.0 to 1.9 mole equivalents of p-toluenesulfonic acid and about 0.1 to 0.9 mole equivalents of sulfuric acid, is hydrate of a mixed acid salt formed form an arbitrary combination of about 1.0 to 1.5 mole equivalents of p-toluenesulfonic acid and about 0.2 to 0.6 mole equivalents of sulfuric acid. More preferable is hydrate of a mixed acid salt formed from an arbitrary combination of about 1.2 to 1.3 mole equivalents of p-toluenesulfonic acid and about 0.4 to 0.5 mole equivalents of sulfuric acid or, hydrate of a mixed acid salt formed from an arbitrary combination of about 1.1 to 1.4 mole equivalents of p-toluenesulfonic acid and about 0.3 to 0.7 mole equivalents of sulfuric acid. Further preferable is hydrate of a mixed acid salt formed from an arbitrary combination of about 1.3 mole equivalents and about 0.4 to 0.5 mole equivalents of sulfuric acid. An another preferred embodiment is a mixed crystal of hydrate of p-toluenesulfonic acid-sufuric acid mixed acid salt represented by the above arbitrary combination, or a crystalline solid of hydrate of a mixed acid salt formed from about 1 mole equivalent of p-toluenesulfonic acid and about 0.5 mole equivalents of sulfuric acid.

As the solvent for forming the solvates, water, ethanol, 2-propanol, methyl acetate, ethyl acetate, n-propyl acetate, 1,2-dimethoxyethane, methyl isobutyl ketone, acetonitrile or the like is exemplified. Preferable is water, ethanol or 2-propanol. More preferable is water. The preferred amount of the solvate is about 0.5 to 20 mole equivalents, more preferable is about 5 to 17 mole equivalents. The water containing hydrate is preferably crystal water, may be contained water as a residual solvent such as adhered water.

The content of water of the present invention, for example, can be selected from the range of about 5 to 20 wt %, may be about 10 to 20 wt %, or also about 10 to 20 wt %. Moreover the content of water thereof, for example, can be selected from the range of about 0.5 to 20 mole equivalents, about 5 to 17 mole equivalents, or also 6 to 12 mole equivalents relative to the compound (IA). In particular, the stabilities of a lot of the crystalline solid of the present invention are improved dependent on increasing the content of water thereof.

The acid addition salt or its solvate, preferably the crystalline solid thereof is crystallized by stirring or leaving to stand for several hours to several days while cooling to about −5 to 5° C. as necessary after addition of generally about 0.5 to 50 mole equivalents of acid to the solution of the compound (IA) by dropwise at about 0° C. to room temperature. The preferred amount of acid is about 5 to 40 mole equivalents, more preferable is about 10 to 30 mole equivalents. The solvent is preferably acetonitrile, acetone, water, ethanol, 2-propanol or a two or more mixed solvent selected from them, more preferably acetonitrile, water, or the mixed solvent thereof. The preparation of the crystalline solid of the solvate is carried out by dissolving the acid addition salt of the compound (IA) into a solubilizing solvent containing the solvent to be solvated at least at about 0° C. to room temperature, and stirring or leaving to stand the solution at about 0° C. to room temperature for several hours to three days. It can be collected from a solvent by the ordinally separating mechanisms, such as filtration or centrifugal separation, and isolated by the ordinary refining means, such as washing and drying.

The "crystalline solid" used in this description means a solid having a structure that atoms, ions, or molecules constituting the solid are regularly aligned, as it turned out that a solid has periodicity or anisotropic nature. The "single phase crystal" means a crystalline solid consisting of a single component or a single structure. The "mixed crystal" means a mixture of two or more kinds of single phase crystals, or a crystalline solid constituting the periodic structure by two or more substances which chemical components are different. "A crystalline solid constituting the periodic structure by two or more substances which chemical components are different" includes, for example, 1) a crystalline solid crystallographically forms a homogeneous solid phase, and it is a chemical mixture that ingredient substances are mixed in various ratio (e.g.: solid solution consisting of a non-metallic or a combination of metallic and non-metallic), 2) a crystalline solid is constituted by two or more kinds of substances on different chemical components, and a part of the periodic structure thereof is substituted with another chemical component substances, 3) a crystalline solid that the substrate atoms or molecules penetrate into the gap of the periodic structure composed of two or more kinds of substances on different chemical components. Namely, "crystalline solid" includes "single phase crystal" and "mixed crystal". Without a mention in particular, the "crystal" is the same meaning as the "crystalline solid". The degree of crystallinity of a crystalline form, for example, can be measured by a number of techniques including an X-ray powder diffraction measurement, a dynamic vapor sorption measurement, differential scanning calorimetry, solution colorimetric measurement, dissolution profile etc.

The crystalline solid of the present invention may be a single crystal, a twin crystal, a polycrystal and the like, generally it is often a single crystal or a mixed crystals thereof. A crystalline form (outline) is not particularly limited, for example, it may be a triclinic crystal, a monoclinic crystal, orthorhombus (orthorhombic crystal), tetragonal crystal, cubic crystal, trigonal crystal (rhombohedron), hexagonal crystal or the like, and also may be a spherulite, skeleton crystal, dendrite crystal, needle crystal (e.g. crystal whisker) or the like. The size of the crystal is not particularly limited, for example, the average particle diameter of the crystal is 0.5 μm to 1 mm, preferably about 1 to 500 μm based on a laser diffraction method.

Moreover, a crystalline solid of an acid addition salt of the compound (IA) or its solvate may come into being adsorption of the moisture depending on a change in relative humidity, as it turned out that its water of hydration may change. Namely, it may be a crystalline solid that water molecules in air can easily move in and out through its crystal lattice as crystal water depending on the external humidity change. As regards such crystalline solids, even when the X-ray powder diffraction pattern thereof have been slightly changed along with the change of their water content, these crystalline solid can be interpreted the substantial same crystalline solid as long as they have characteristic peaks described herein. The water may be either the crystal water or the residual solvent such as adhered water. Further the crystalline solid may be either a single phase crystal or a mixed crystal.

A crystalline solid of an acid addition salt of the compound (IA) or its solvate is preferably characterized by diffraction peaks in the X-ray powder diffraction spectrum.

The present invention also includes a mixed crystal composed of a number of crystalline solids of the compound (IA) having diffraction peaks at different diffraction angles mutually in an X-ray powder diffraction spectrum. The mixed crystals include a single phase crystal characterized by at least the following diffraction peaks.

In the present specification, the diffraction peak may be a single sharp peak (singlet type), one of gentle peak (broad form), or about two to five of multiple peak (doublet type, triplet type, quartet type, quintet type), and yet usually it is often one sharp peak.

The crystalline solid of 8.5 hydrates of 2 mole equivalents of p-toluenesulfonic acid salt of the compound (IA) shows an X-ray powder diffraction pattern as shown in FIG. 1, and shows characteristic peaks at diffraction angle (2θ): 8.1±0.2°, 13.3±0.2°, 17.4±0.2°, 19.1±0.2° and 21.3±0.2°.

The crystalline solid of the mixed acid salt of the compound (IA), wherein the mixed salt is formed from 1 mole equivalent of p-toluenesulfonic acid and 1 mole equivalent of hydrochloric acid, shows an X-ray powder diffraction pattern as shown in FIG. 2, and shows characteristic peaks at diffraction angle (2θ): 8.5±0.2°, 10.2±0.2°, 20.3±0.2°, 24.6±0.2° and 26.2±0.2.

The crystalline solid of the mixed acid salt of the compound (IA), wherein the mixed salt is formed from 1 mole equivalent of p-toluenesulfonic acid and 1 mole equivalent of hydrobromic acid, shows an X-ray powder diffraction pattern as shown in FIG. 3, and shows characteristic peaks at diffraction angle (2θ): 8.5±0.2°, 10.3±0.2°, 16.6±0.2°, 24.7±0.2° and 26.3±0.2°.

The crystalline solid of 2 mole equivalents of benzenesulfonic acid salt of the compound (IA) shows an X-ray powder diffraction pattern as shown in FIG. 5, and shows characteristic peaks at diffraction angle (2θ): 10.3±0.2°, 13.3±0.2°, 16.5±0.2°, 19.2±0.2° and 20.8±0.2°.

The crystalline solid of the mixed acid salt of the compound (IA), wherein the mixed acid is formed from 1.05 mole equivalents of p-toluenesulfonic acid and 0.65 mole equivalents of sulfuric acid, shows an X-ray powder diffraction pattern as shown in FIG. 16, and shows characteristic peaks at diffraction angle (2θ): 8.4±0.2°, 10.2±0.2°, 13.1±0.2° and 20.4±0.2°.

The crystalline solid of the mixed acid salt of the compound (IA), wherein the mixed acid is formed from 1.0 mole equivalent of p-toluenesulfonic acid and 0.5 mole equivalents of sulfuric acid, shows an X-ray powder diffraction pattern as shown in FIG. 17, and shows characteristic peaks at diffraction angle (2θ): 8.3±0.2°, 10.1±0.2°, 13.0±0.2°, 16.5±0.2° and 20.3±0.2°.

The crystalline solid of hydrate of 2 mole equivalents p-toluenesulfonic acid salt of the compound (IA) shows an X-ray powder diffraction pattern as shown in FIG. 18, and shows characteristic peaks at diffraction angle (2θ): 5.3±0.2°, 8.0±0.2°, 13.0±0.2°, 19.0±0.2° and 20.3±0.2°.

The type I crystal (:the crystalline solid of hydrate of the mixed acid salt of the compound (IA), wherein the mixed acid is formed from 1.3 mole equivalents of p-toluenesulfonic acid and 0.35 mole equivalents of sulfuric acid) shows an X-ray powder diffraction pattern as shown in FIG. 4, 5, or 7 to 15, shows characteristic peaks at diffraction angle (2θ): 8.2±0.2°, 8.9±0.2°, 10.1±0.2°, 11.4±0.2°, 13.0±0.2°, 20.3±0.2° and 26.2±0.2°. In particular, diffraction angel (2θ): 8.2±0.2°, 10.1±0.2°, 13.0±0.2° and 20.3±0.2° are more characteristic peaks.

A crystalline solid of an acid addition salt of the compound (IA) or its solvate is preferably at least one peak selected from diffraction angle (2θ): 8.2±0.2°, 10.1±0.2°, 13.0±0.2° and 20.3±0.2°.

A crystalline solid of an acid addition salt of the compound (IA) or its solvate is preferably at least one peak selected from diffraction angle (2θ): 8.2±0.2°, 8.9±0.2°, 10.1±0.2°, 11.4±0.2°, 13.0±0.2°, 20.3±0.2° and 26.2±0.2°.

A crystalline solid of an acid addition salt of the compound (IA) or its solvate is preferably at least one peak selected from diffraction angle (2θ): 8.2±0.2°, 8.9±0.2°, 10.1±0.2°, 11.4±0.2°, 13.0±0.2°, 19.9±0.2°, 20.3±0.2°, 21.5±0.2° and 26.2±0.2°.

A crystalline solid of an acid addition salt of the compound (IA) or its solvate is preferably at least one peak selected from diffraction angle (2θ): 8.2±0.2°, 8.9±0.2°, 10.1±0.2°, 13.0±0.2°, 16.5±0.2°, 17.0±0.2°, 17.9±0.2°, 19.0±0.2°, 20.3±0.2° and 26.2±0.2°.

The crystalline solid of the present invention is usually prepared by crystallizing the compound (IA) in the oversaturated state after dissolving the compound (IA) in the crystallization solvent and/or acid. The crystallization method (the method for making a transition to the oversaturated state) is not particularly limited, for example, an evaporation method (a method for evaporating the crystallization solvent from the crystallization solution), a cooling method (a method for cooling the crystallization solution or the solution of the compound (IA), an antisolvent crystallization method (a method for adding an antisolvent of the compound (IA) to the crystallization solution), a seed crystal addition method (a method for adding a seed crystal containing the compound (IA) to the crystallization solution) and the like can be exemplified. For example, a crystalline solid of the present invention can be manufactured by a seed crystal addition method of crystallizing the compound (IA) by adding a seed crystal to a solution dissolved the compound (IA) in the crystallization solvent and/or the acid, after obtaining the seed crystal from a evaporation method (a method of crystallization from the crystallization solution in the oversaturated state obtained by evaporating the crystallization solution (or the solution) containing the compound (IA) and the crystallization solvent from the crystallization solvent) or a cooling method (a method of crystallization from the crystallization solution in the oversaturated state obtained by cooling the crystallization solution (or the solution) containing the compound (IA) and the crystallization solvent)
According to this method, the crystalline solid can be manufactured efficiently.

As a crystallization solvent, $C_{1-4}$ alkanol such as methanol, ethanol, 1-propanol, 2-propanol, 1-butanol, 2-butanol etc.; $C_{5-6}$ alkane such as pentane, hexane etc.; di-$C_{1-4}$ alkyl-ether such as diisopropylether; $C_{2-4}$ ketone such as acetone, methyl ethyl ketone; amide solvent such as dimethylacetoamide, N-methylpyrrolidone etc.; acetonitrile, water etc. can be exemplified. These crystallization solvent can be used alone or as a mixed solvent.

The amount of the crystallization solvent, for example, is 1 to 100 mL, preferably 2 to 60 mL, and more preferably about 5 to 55 mL, for 1 g of the compound (IA).

Crystallization operation may be at once, and yet may be repeated several times in order to improve the purity of the crystalline solid. The crystallized material obtained by crystallization is generally purified (separated from amorphous material) by the separating means such as filtration and centrifugal separation. The separated crystallized materials may be dried.

The drying method may be any of natural drying, air-drying, and drying under reduced pressure. For example, drying under reduced pressure may be at about 1 to 100 hpa, preferably about 1 to 40 hpa (e.g. 1.5 to 10 hpa, 10 to 35 hpa). The drying temperature, for example, may be room temperature to under heating, preferably about 20 to 80° C. The drying time, for example, may be about 0.5 to 48 hours, preferably about 0.5 to 24 hours.

Additionally, a crystalline solid of an acid addition salt of the present invention or its solvate can be synthesized by adding an acid to the reaction solution or the solution such as a column eluate containing the compound (IA). In detail, the crystalline solid of an acid addition salt of the compound (IA) can be obtained by adding about 2 to 40 wt % of the acid to the reaction solution or a column eluate containing the compound (IA) and adding the seed crystal as needed, and cooling to at about −5 to 5° C., and then being stirred or leaving to stand for about 1 hour to about 4 days to crystallize the compound (IA), and being washed with cold water or the acid, and dried at normal pressure or reduced-pressure for about 0.5 to 10 hours. Or, the different crystalline solid of an acid addition salt from the crystalline solid of the acid addition salt of the present invention (for example, it is Z crystal) can be also obtained by dissolving or suspending Z crystal in a crystallization solvent, and performing salt exchange of the compound (IA) by adding a different acid, and then crystallized from the resulting solution.

For example, the crystalline solid of hydrate of 2 mole equivalents of p-toluenesulfonic acid salt of the compound (IA) is obtained as follows. Namely, to an acetonitrile solution, an acetone solution, an aqueous solution or a mixed solution thereof containing the compound (IA) is added an aqueous solution of about 2 to 20 mole equivalents of p-toluenesulfonic acid to dissolve it, and the resulting solution is crystallized by leaving to stand at room temperature to about 0 to 5° C. for about 1 to 4 days. An obtained crystalline solid is washed with cold water and air-dried at room temperature for about 1 to 3 hours to yield the desired crystalline solid of hydrate of 2 mole equivalents of p-toluenesulfonic acid salt.

Moreover, the type I crystal of the compound (IA) (: the mixed crystal of hydrate of a mixed acid salt formed from 1.3 mole equivalent of p-toluenesulfonic acid and 0.35 mole equivalents of sulfuric acid) is obtained as follows. Namely, the crystalline solid of hydrate of 2 mole equivalents of p-toluenesulfonic acid of the compound (IA) is dissolved in a mixed solution of sulfuric acid and water, and the resulting solution is crystallized by leaving to stand at 0 to 5° C. for about 1 to 4 days, the obtained crystalline solid is washed with cold water and air-dried at room temperature for about 0.5 to 2 hours to yield the type I crystal. Or, to the mixed solution of acetonitrile and water containing the compound (IA) is added sulfuric acid and a seed crystal as needed, the resulting solution is colded to about −5 to 5° C., and stirred or leaving to stand for about 1 hour to about 4 days to crystallize. The obtained crystalline solid is washed with cold water or the acid and dried at normal pressure or reduced pressure for about 0.5 to 10 hours to yield the type I crystal.

The type I crystal of the compound (IA) can include even more about 0.01 to 0.1 mole equivalents of p-toluenesulfonic acid and/or about 0.01 to 0.1 mole equivalents of sulfuric acid as residual acid in some cases. The residual acid may sometimes be contained in a form to be adhered to the crystal or incorporated into the crystal.

Further, a crystalline solid of an acid addition salt of the present invention can be synthesized by salt exchange from an acid addition salt crystal of different composition. For example, the crystalline solid of hydrate of 2 mole equivalents of p-toluenesulfonic acid salt of the compound (IA) is dissolved or suspended in the crystallization solvent and/or the acid, and added the corresponding acid and cooled to about −5 to 5° C. The resulting solution is crystallized while performing salt exchange by stirring or leaving to stand for about 1 hour to about 4 days. The obtained crystalline solid is washed with cold water or the acid, and dried at normal pressure or reduced pressure for about 0.5 to 10 hours to be able to yield a crystalline solid of an acid addition salt of the present invention.

As the preferred amount of acid in the manufacturing method of the type I crystal of the compound (IA) (: a mixed crystal of hydrate of a mixed acid salt formed from 1.3 mole equivalents of p-toluenesulfonic acid and 0.35 mole equivalents of sulfuric acid), p-toluenesulfonic acid monohydrate is about 2 to 3 wt %, more preferably about 2.2 to 2.5 wt % of p-toluenesulfonic acid monohydrate for the solution containing the compound (IA), and sulfuric acid is about 4.5 to 7 wt %, more preferably about 5 to 6 wt % for the solution containing the compound (IA). Or, for 1 pts·wt. of the compound (IA), p-toluenesulfonic acid monohydrate is about 1.2 to 1.5 pts·wt., and 75% sulfuric acid is about 2.7 to 3.5 pts·wt.

Specifying methods of the crystalline solid of the present invention are illustrated below.

If there is no reference in particular, the numerical value of the description and claims is a near value. A numerical change originates in a device calibration, a device error, the purity of a substance, a crystal size, a sample size, and the other factors.

The crystalline solid of the present invention is clearly identified by spectrophotometrical probes (e.g. an X-ray diffraction, an infrared spectrum, a Raman spectrum, and solid NMR).

The crystalline solid of the compound (IA), its acid addition salt, or a solvate thereof is preferably identified by an X-ray powder diffraction profile. The characteristic diffraction peaks are selected from preferably about 10, more preferably about 5, further preferably about 3 in a diffraction patterns.

Since an error in the range of ±0.2° may occur in diffraction angles (2θ) in X-ray powder diffraction, in general, the value of the above diffraction angle should be understood as including value in a range of around ±0.2°. Therefore, the present invention includes not only the crystalline solids whose diffraction angles of the peaks in X-ray powder diffraction perfectly match, but also crystals whose diffraction angles of the peaks match within an error of around ±0.2°.

In general, it is known that the relative intensities and absolute intensities of various peaks shown in the Tables and Figures below may vary to a number of factors such as orientation effects of crystalline solids in the X-ray beam, influence of coarse particles, the purity of the material being analyzed, or the degree of crystallinity of the sample. The peak position may also shift for variations in sample height. Furthermore, measurements using a different wavelength will result in different shifts according to the Bragg equation ($n\lambda = 2d \sin \theta$). Such further XRPD patterns obtained by using a different wavelength are within the scope of the present invention.

The characteristic diffraction peaks as used herein are peaks selected from the observed diffraction pattern. In order to distinguish between multiple crystalline solid, a peak which is shown for the crystal and not shown for the other crystalline solid becomes a more preferable characteristic peak than the size of a peak when the crystalline solid is specified. The crystalline solid can be characterized by one or two peak(s) if it is such characteristic peak(s).

In particular the type I crystal can be distinguished from the other crystalline forms (e.g., anhydrous etc.) disclosed herein by the presence of characteristic diffraction peaks. Further, by comparing the chart obtained by measuring, if these characteristic peaks coincide, the X-ray powder diffraction spectrum can be said to substantially match up. The water content of the type I crystal can be changed by the relative humidity, and the hydration state thereof can be changed. The type I crystals having such as the different water content have the characteristic peaks in common as shown in FIG. 4, 5 or 8 to 15.

The characteristic peaks in common are at least three peaks selected from diffraction angle (2θ): 8.2±0.2°, 8.9±0.2°, 10.1±0.2°, 11.4±0.2°, 13.0±0.2°, 19.9±0.2°, 20.3±0.2° and 26.2±0.2°. The more preferable characteristic peaks in common are at least three peaks selected from diffraction angle (2θ): 8.2±0.2°, 10.1±0.2°, 13.0±0.2° and 20.3±0.2°.

Single crystal structure analysis (See Toshio Sakurai et al. "A guidance of X-ray structural analysis" Shokabo issue (1983), Stout & Jensen et al. X-Ray Structure Determination: A Practical Guide, Macmillan CO., New York (1968)) is one method of identifying a crystal, it is possible to obtain a crystallographic parameters of the crystal, further an atom coordinate (value showing the spatial positional relation of each atoms) and a three dimensions structural model. Single crystal structure analysis is useful for identifying the structure of crystals of a complex such as the present invention.

Infrared absorption spectroscopy is a methods to determine the degree of absorption of infrared when it goes through samples with each wavenumber. Infrared absorption spectrum is usually shown in a graph of wavenumber on the horizontal axis and transmittance or absorbance on the vertical axis. The wavenumber and transmittance (or absorbance) of an absorption peak may be readable from the graph, or a calculated value by a data processing equipment can be used. The infrared absorption spectrum is determined by a chemical structure of the substance. Therefore, the substance may be determined and fixed quantity by measuring absorption of various wavenumbers. Crystal polymorphs can be distinguished by comparing the absorption bands of the characteristic functional groups for the crystal polymorph, that is, mainly the functional groups related to a hydrogen bond in the crystal structure such as C=O bond, OH bond, NH bond and the like, and the other characteristic functional groups such as C—X (halogen), C=C, C≡C and the like. The absorption bands for characteristic functional group are selected form about 20, more preferably about 10, the most preferably about 5 absorption peaks. Usually, the absorption spectrum of a sample is measured in a range of 4000 cm$^{-1}$ to 400 cm$^{-1}$ of wavenumber. Infrared absorption spectroscopy is carried out under the same operation conditions in which resolution of device, and scale and accuracy of wavenumber are confirmed.

Since an error in the range of ±2 cm$^{-1}$ may occur in absorption bands (cm$^{-1}$) in infrared absorption spectroscopy, in general, the value of the above absorption peaks should be understood as including values in a range of around ±2 cm$^{-1}$. Therefore, the present invention includes not only crystals whose absorption peaks in infrared absorption spectroscopy perfectly match, but also crystals whose absorption peaks match within an error of around ±2 cm$^{-1}$.

Infrared absorption spectroscopy includes a measurement method for potassium bromide tablets, solution, paste, liquid membrane, thin film or gas samples, ATR method, diffuse reflection method and the like. Among them, ATR method (Attenuated total reflection) is called as a total reflection measurement method and one of the reflection methods. This is a method that a sample is adhered to surface of prism made from a substance with high refractive index such as KRS-5, light is entered in a prism at an optimal angle or more, and fully-reflected light is measured on the border of prism and sample to obtain the absorption spectrum. Because one of the conditions to measure by the ATR method is that the refractive index of prism is larger than that of the sample, it is necessary to change material of prism depending on the sample. Additionally, the other condition is that the prism and sample must be adhered. Therefore, the ATR method is suitable to measure liquid, powder, plastic, soft rubber or the like, and has advantage to be able to measure without chemical or physical treatment of a sample. On the other hand, a diffuse reflection method is a method to measure as powder without making a potassium bromide tablet in measurement for powder samples. When a sample is exposed to light, light which regularly reflect on surface of powder and goes outside and diffuse reflection light (scattering light) which enters inside of the sample, repeats transmission and diffusion, and then go on the surface are occurred. The latter is used for the diffuse reflection method to obtain an absorption spectrum.

Raman spectrum is shown characters of molecular or lattice vibrations. The origin is a non-resistance collision of a molecular and a photon which is light particle including light ray. The collision of the molecular and photon brings exchange of energy. As a result, energy and then wavelength of the photon change. That is, Raman spectrum is a set of lines in extremely narrow spectrum emitted from the target molecule when it is exposed to the incident light. Width of each spectrum line is largely affected by spectrum width of the incident light and then light source strictly in one color, for example, laser is used. Wavelength of each Raman line is shown by wavenumber shift from the incident light and it is difference between the recioricals of wavelengths of Raman line and incident light. Raman spectrum is to measure vibration state of molecular and determined by the molecular structure.

Since an error in the range of ±2 cm$^{-1}$ may occur in absorption bands (cm$^{-1}$) in Raman spectrum, in general, the value of the above absorption peaks should be understood as including values in a range of around ±2 cm$^{-1}$. Therefore, the present invention includes not only crystals whose absorption peaks in Raman spectrum perfectly match, but also crystals whose absorption peaks match within an error of around ±2 cm$^{-1}$.

Solid state $^{13}$C-NMR (Nuclear magnetic resonance) is useful to identify a crystal form because (i) the number of spectra corresponds to carbon number of the compound, (ii) range of chemical shift is wide compared with $^1$H-NMR, (iii) signals are sharp compared with Solid state $^1$H-NMR, (iv) chemical shift does not change even if an additive is include, or the like. It is expected that the observed chemical shifts slightly change according to a used specific spectrometer or a sample preparation technique of an analyst. The error span in a solid state $^{13}$C-NMR spectrum is approximately ±0.5 ppm.

The crystalline solid of the present invention may be identified by methods of the thermal analysis.

DSC (differential scanning calorimetry), one of the main measuring methods for thermal analysis, is a method of measuring the thermal properties of the substance as an aggregate of an atom(s) and a molecule(s). A differential scanning calorimetry curve can be obtained by measuring temperatures or change of heat capacity over tie of a pharmaceutical active ingredient by DSC, and plotting the obtained data to temperatures or times. From a differential scanning calorimetry curve, the information about the onset temperature, melting endothermic maximum and enthalpy of a pharmaceutical active ingredient can be obtained.

As to DSC, it is known that the observed temperature can depend on rate of temperature change, the sample preparations techniques or the specific devices. Thus, "melting point" in the DSC refers to the onset temperature less affected of the sample preparation techniques. The error span in the onset temperature obtained from a differential scanning calorimetry curve is approximately ±2° C.

TG/DTA (Thermogravimeric/Differential Thermal Analysis) is one of the major measuring methods of a thermal analysis, and is the method of measuring the weight and the thermal property of a substance as an aggregate of an atom and a molecule. TG/DTA is the method of measuring change of the weight and the quantity of heat concerning the temperature or time of an active pharmaceutical ingredient, and TG (thermo gravity) and a DTA (Differential Thermal Analysis) curve are obtained by plotting the obtained data to temperature or time. From TG/DTA curve, the information on the weight about decomposition of an active pharmaceutical ingredient, dehydration, oxidation, reduction, sublimation, and evaporation and quantity-of-heat change can be acquired.

It is known that the temperature and the weight change observed can be dependent on heating rate, the sample preparation technique to be used, and a specific device about TG/DTA. In authorization of the identity of crystal, an overall pattern is important and may change with measurement conditions to some degree.

Dynamic vapor sorption (DVS) is a gravimetric technique that measures how quickly and how much of water is absorbed and desorbed by a sample in several relative humidity (RH).

A degree of water absorption is calculated by weight change in controlled humidity increased from 0% RH to 95% RH stepped 5% or 10%. Similarly, a degree of water desorption is calculated in humidity decreased from 95% RH to 0% RH.

An absorption-desorption isotherm is obtained by plotting a value of weight change in each humidity. These results can provide the information of adhered water absorption and desorption. When the anhydrate crystal transforms to hydrate crystal by humidity, the results of measurement indicate transformation humidity and amount of crystal water.

The results of absorption and desorption behavior of adhere water or crystal water are affected by particle diameter, crystallinity and crystal habit.

The sodium salt of the compound (IA) or a solvate thereof is obtained by adding a sodium source such as sodium hydroxide or sodium bicarbonate to the solution containing the compound (IA) to adjust the pH to about 5 to 6.5, and then concentrating under reduced pressure and/or lyophilizing. The sodium salt or a solvate thereof has the advantageous characteristics such as: 1) high solubility in water, 2) good stability against heat, moisture, dissolution and/or light, 3) small specific volume, 4) difficult charged, 5) it can be manufactured in a low environment burden condition, 6) it can be mass produced, 7) it can be controlled to a suitable pH range to administer into a vein without vascular pain, 8) it has a suitable property for lyophilized formulation, or 9) fast dissolution rate in water, and the like.

The sodium salt of the compound (IA) is useful as pharmaceutical active ingredient or its raw material. Although the sodium salt can be produced from the compound (IA) directly, it can be also obtained by lyophilizing a aqueous solution containing the acid addition salt of the compound (IA) or a solvate thereof, preferably a crystalline solid thereof and sodium hydroxide and optionally other additives (e.g. sugars, pH modifiers, sodium chloride or magnesium chloride) in accordance with techniques well known in the art. The sodium salt of the compound (IA) is preferably non-crystalline, that is an amorphous form, and its water solubility is very high.

As the condition for lyophilizing, a condition for freezing is at about −50 to −3° C. for 0.5 to 5 hours, preferably about −40 to −5° C. for 1 to 4 hours, and a condition for annealing is about −40 to −20° C. for 1 to 3 hours, preferably about −35 to −25° C. for 1.5 to 2.5 hours, a condition of primary drying is at about −50 to −10° C. for 0.1 to 150 hours at about 5 to 20 Pa in vacuum pressure, preferably at about −40 to −20° C. for 0.5 to 130 hours, at 7.5 to 15 Pa in vacuum pressure, and a condition of secondary drying is at about 15 to 70° C. for 1 to 7 hours at 5 to 20 Pa in vacuum pressure, preferably at about 20 to 65° C. for 1.5 to 6.5 hours at 5 to 20 Pa in vacuum pressure.

The formulation of the present invention after lyophilizing is administered after adding a solution such as a distilled water for injection, normal saline solution or glucose solution at the time of use to dissolve. The pharmaceutical composition of the present invention exhibits a strong antibacterial spectrum against Gram-positive bacteria and Gram-negative bacteria, especially β-lactamase producing Gram-negative bacteria, and it does not exhibit cross-resistance with existing cephem drugs and carbapenems.

The compound (IA) of the present invention, its sodium salt, its acid addition salt, or or a solvate thereof has a broad antibacterial spectrum, especially it has strong antibacterial activity against β-lactamase producing Gram-negative bacteria (e.g.: Class B type of metallo-β-lactamase producing Gram-negative bacteria). Thus, it is effective for prevention or therapy against a variety of diseases caused by causative bacteria in a variety of mammals including humans, for example, airway infectious diseases, urinary system infectious diseases, respiratory system infectious diseases, sepsis, nephritis, cholecystitis, oral cavity infectious diseases, endocarditis, pneumonia, bone marrow membrane myelitis, otitis media, enteritis, empyema, wound infectious diseases, opportunistic infection and the like.

Since the salt of the present invention or its solvate, and a crystalline solid thereof has high solubility, it is particularly suitable as an injection. Moreover, the salt of the present invention or its solvate, and a crystalline solid thereof also has advantages as pharmacokinetics of high blood concentration, long duration of effect and/or remarkable tissue migration and the like. Furthermore, the salt of the present invention or its solvate and a crystalline solid thereof has high stability in human plasma, and is extremely effective as a medicine. Additionally, since the salt of the present invention or its solvate and a crystalline solid has advantageous characteristics in manufacturing sides such as: (1) good stability against heat, moisture, dissolution and/or light, (2) its storage stability and/or coloring stability is good, (3) it is possible to provide a high purity drug substance, (4) easy operation of filtration or centrifugation, (5) it improves the solvent removal efficiency, (6) small specific volume, (7) it is difficult to charge, (8) it can be manufactured in a low environment burden condition, (9) it can be mass produced, and the like, it is useful as a source material for manufacturing medicine.

The salt of the present invention or its solvate and a crystalline solid thereof can be administered to a patient directly or a pharmaceutical composition in which the crystalline solid described above is blended with a pharmaceutical carrier or excipient can also be administered. The technical information for the formulation and administration of the drug can be found out to "Remington's Pharmacological Sciences" Mack Publishing Co., Easton, Pa. the latest version.

A pharmaceutical composition of the present invention can be administered orally or parenterally. Methods for parenteral administration include dermal, subcutaneous, intravenous, intraarterial, intramuscular, intraperitoneal, transmucosal, inhalation, transnasal, ophthalmic, inner ear or vaginal administration and the like.

In case of oral administration, any forms, which are usually used, such as oral solid formulations (e.g., tablets, powders, granules, capsules, pills, films or the like), oral liquid formulations (e.g., suspension, emulsion, elixir, syrup, lemonade, spirit, aromatic water, extract, decoction, tincture or the like) and the like may be prepared according to the usual method and administered. Wherein the tablets can be sugar-coated tablets, film-coated tablets, enteric-coating tablets, sustained-release tablets, troche tablets, sublingual tablets, buccal tablets, chewable tablets or orally disintegrated tablets. Powders and granules can be dry syrups. Capsules can be soft capsules, micro capsules or sustained-release capsules.

In case of parenteral administration, any forms, which are usually used, such as injection (e.g., intravenous injection, intramuscular injection, intravenous drip, ampule for subcutaneous injection, vials, solutions, suspensions or the like), local administration agent (e.g., ear drops, nasal drops, eye drops, ointments, emulsions, sprays, aerosols, inhalants, suppositories, or the like), external preparations (e.g., lotions, injection agents, coating agents, mousewashs, enemas, ointments, plasters, jellies, creams, patches, cataplasms, external powders, suppositories or the like) and the like can be preferably administrated. Wherein injections can be emulsions whose type is O/W, W/O, O/W/O, W/O/W or the like. In particular, injections can be prepared by using a powder-filled formulation or a lyophilized formulation containing the salt of the present invention or its solvate, or a crystalline solid thereof. Preferably, it is a lyophilized formulation containing the salt of the present invention or its solvate or a crystalline solid thereof. The lyophilized formulation of the present invention can be used as an aqueous solution for application such as injection. In this case, the salt or the crystalline solid having good solubility in water or good dissolution rate in water is preferable. Preferably, it is the sodium salt of the compound (IA).

The pharmaceutical composition may be manufactured by mixing an effective amount of the compound of the present invention with various pharmaceutical additives suitable for the formulation, such as excipients, binders, disintegrants, lubricants, and the like. Furthermore, the pharmaceutical composition can be for pediatric patients, geriatric patients, serious cases or operations by appropriately changing the effective amount of the compound of the present invention, formulation and/or various pharmaceutical additives. The pediatric pharmaceutical compositions are preferably administered to patients under 12 or 15 years old. In addition, the pediatric pharmaceutical compositions can be administered to patients who are under 27 days old after the birth, 28 days to 23 months old after the birth, 2 to 11 years old, 12 to 16 years old, or 18 years old. The geriatric pharmaceutical compositions are preferably administered to patients who are 65 years old or over.

Although a suitable route for administration is not limited, it is possible to include oral, intrarectal, transmucosa, enteral, intramuscular, subcutaneous, intraspinal, intrathecal, direct intraventricular, intravenous, intraperitoneal, intranosal, intraocular administration, and injection. Intravenous injection is preferable. The pharmaceutical composition of the present invention can be prepared by a method well known in the technical field such as a conventional mixing, dissolution, granulation, sugar-coating, powderization, emulsifying, encapsulation, packing and lyophilization processes.

The pharmaceutical composition used in the present invention can be formulated by a known method using one or more of pharmaceutically acceptable carrier including an excipient and an additive which make easy to prepare pharmaceutically allowable formulation comprising the crystal of the present invention. A suitable formulation depends on a selected route of administration. The above formulation may contain appropriate additives: for example, excipients, auxiliaries, stabilizers, wearing agents, emulsifiers, the other additives depending on the dosage form. It is necessary that these additives are available pharmaceutically and pharmacologically, and they do not have an effect on the cephalosporin derivatives. For example, the formulations for oral include lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid or the like. The formulations for parenteral may include solvent (alcohol, buffer, methyl oleate, water etc.), buffering agents, dispersing agents, solubilizing agents, stabilizing agents (methyl p-hydroxybenzoate or ethyl p-hydroxybenzoate, sorbic acid etc.), absorption enhancers (mono- or di-octanoate esters etc.), anti-oxidants, fragrances, analgesic agents, suspending agents, side effect inhibitor, action-enhancing substances (absorption excretion modifiers, anti-enzymatic degradation agents, β-lactamase inhibitors, other types antimicrobial agents etc.).

Besides the above additives, anti-oxidant, buffers, soothing agents and preserving agents can be added to the salt of the present invention or its solvate or a crystalline solid thereof, whose additives can be stabilized them and be used for injection and are described in Japanese Pharmacopoeia, the Japanese Pharmaceutical Codex, the Pharmaceutical Additives Standards and Food Additives Compendial. Specifically, as an antioxidant, sodium bisulfite, sodium pyrosulfite, ascorbic acid and the like are included. As a buffers, citrate, acetate, phosphate and the like are included. As a soothing agent, procaine hydrochloride, lidocaine hydrochloride, chlorobutanol, benzyl alcohol and the like are included. As a preservatibe, methyl parahydroxybenzoate, propyl parahydroxybenzoate, ohenol, cresol, benzyl alcohol, chlorobutanol, chlorocresol and the like are included.

When administering by injection, the salt of the present invention or its solvate, or a crystalline solid thereof can be administered after dissolving it in an aqueous solution, preferably, in Ringer's solution or a buffer solution such as physiological saline, which are physiologically acceptable. Moreover, bases for pH adjustment (e.g., sodium hydroxide etc.) and the like may be used. In a case of transmucosal administration, it can be achieved by using a penetrating agent suitable for the target barrier. The penetrating agent conventionally used in the technical field can be used. As a carrier in a case of use as capsules, granules, tablets, publicly known excipients (e.g., starch, lactose, sucrose, calcium carbonate, calcium phosphate etc.), binders (e.g., starch, gum arabic, carboxymethyl cellulose, hydroxypropyl cellulose, crystalline cellulose etc.), lubricants (e.g., magnesium stearate, talc etc.) and the like are included.

The pharmaceutical composition containing the salt of the present invention or its solvate or a crystalline solid thereof can also include appropriate solids or carriers of gel phase or excipients. As these carriers or excipients, for example, inorganic salt (e.g., sodium chloride, magnesium chloride, calcium carbonate, calcium phosphate etc.), organic salts (e.g., sodium p-toluenesulfonate, sodium gluconate, sodium citrate etc.), sugar or sugar alcohols (e.g., glucose, fructose, sucrose, trehalose, mannitol etc.), acid (e.g., gluconic acid, citric acid etc.), polymers (e.g., starch, cellulose derivatives, gelatin, polyethylene glycol etc.) and the like are exemplified. One or more salt(s) selected from inorganic salts and organic salts and sugar or sugar alcohols are preferable.

Although a pharmaceutical composition containing a salt of the present invention or its solvate or a crystalline solid thereof is obtained by drying after dissolving or suspending the salt of the present invention or its solvate, or a crystalline solid thereof and additives to water, the drying methods should be a drying method that the salt of the present invention or its solvate or a crystalline solid thereof is stable. Specifically, although the suction drying method using an evaporator, spray drying method, freeze-dried method and the like are exemplified, preferably is freeze-drying method. The desirable pharmaceutical composition of the present invention is freeze-dried product.

As a specific method for manufacturing a pharmaceutical composition containing a salt of the present invention or its solvate or a crystalline solid thereof,
1) a salt of the present invention or its solvate or a crystalline solid thereof is put in water for injection to prepare a acidic slurry liquid,
2) to a slurry liquid of 1) is added sodium hydroxide aqueous solution to adjust to pH 5.5 to 6, and then additives are added,
3) water for injection is added to them to adjust their concentration to 5 w/w %, a formulation solution is prepared by sterile filtered the resulting solution,
4) a quantity of the preparation solution of 3) is dispensed in vials or ampoules or the like and lyophilized them to manufacture the desired pharmaceutical composition. The vacuum freeze dryer can be used as a freeze dryer.

Although it is desirable to set the dose of the salt of the present invention or its solvate or a crystalline solid thereof in consideration of the age of the patient, body weight, disease type and degree or administration route and the like, the dose in a case of orally administration is usually 1 μg to 1 g/day, preferably is 0.01 to 200 mg/day, the dose in a case of parenteral administration is usually 1 μg to 10 g/day, preferably 0.1 mg to 10 mg/day. It may be administered once to several times in a day.

EXAMPLES

The present invention is explained in more detail by examples below, but these examples do not limit the present invention. Although an effort to guarantee accuracy about numerical values (for example, quantity, temperature, etc.) is paid, some errors and deviations should be taken into consideration. If not shown in particular, % is weight % of a component, and weight % is weight % of the full weight of a composition, and equivalent is mole equivalent of a component. A pressure is an atmospheric pressure or a pressure near it. A definition of abbreviations used in the present description is as follows: g is a gram, L is a liter, mg is a milligram, mL is a milliliter, and EDC is 1-ethyl-3-(3-dimethylamino propyl) carbodiimido.

(Measurement of an X-Ray Powder Diffraction Pattern)

X-ray powder diffraction measurement of the crystalline solid obtained in each example was performed on any one of the following measurement condition 1 to 3 in accordance with the X-ray powder diffraction method described to General Test Procedures of the Japanese pharmacopoeia. It should be noted that the aluminium plate is used as a sample folder. The peak whose 2-theta (2θ) value is around 38° is the peak of aluminium.

Measurement Condition 1:
(Device)
D-8 Discover (Bruker)
(Operation Method)
Measuring method: Reflection method
The kind of light source: Cu bulb
Operation wavelength: CuK α rays
Tube current: 40 mA
Tube voltage: 40 Kv
Sample plate: Al
Sample range: 3°-40°
Exposure time: 120 s
Measurement Condition 2:
(Device)
TINT TTR III (Rigaku)
(Operation Method)
As to each sample, the following measurement condition was adopted.
Measuring method: Reflection method, parallel method
The kind of light source: Cu bulb
Operation wavelength: CuK α rays
Tube current: 300 mA
Tube voltage: 50 Kv
The angle of incidence of the X-ray (2θ): 4° to 40°
Sampling width: 0.02°
Scan speed: 5°/min
Measurement Condition 3:
(Device)
RINT2100 Ultima+ (Rigaku Corp.)
(Operation Method)
Measuring method: Reflection method
The kind of light source: Cu bulb
Operation wavelength: CuK α rays
Tube current: 40 mA
Tube voltage: 40 Kv
Sample plate: Al
Sample range: 5° to 35°
Sampling width: 0.020°
Scan speed: 30°/min
(Measurement of TG/DTA Data)

About 5 mg of each crystalline solid obtained in each example were measured, and an aluminium pan was stuffed with it and measured in the open system.
(Measurement Conditions)
Device: TG/DTA 6300 by SEIKO
Measurement temperature range: 25° C.-300°
Heating rate: 10° C./min
(Measurement of Solid State $^{13}$C-NMR Spectrum)

The solid state $^{13}$C-NMR spectrum of the crystalline solid obtained in each example can be measured by the following conditions using Varian 600 MHz NMR Systems.
Spectral width: 43103.4 Hz
Acquisition Time: 0.04 s
Sequence: tancpx
Recycle Delay: 10 s
Contact Time: 3 ms
External standard: adamantane (38.52 ppm) or glycine (43.67 ppm)
Measurement temperature: 10° C.
Rotation speed: 20000 rps
Probe: 3.2 mm T3 HX Probe
(Measurement of Dynamic Vapor Sorption)

The dynamic vapor sorption measurement of the crystalline solid obtained in each example was carried out. The sample of about 18.0 mg was measured and transferred to a sample pan, and it was measured. The measurement condition is shown below.
Device: DVS Advantage made by Surface Measurement Systems LTD.
Measurement point: each 5% from RH95% to RH0%.
Temperature: 25° C.
(Method of Measuring the Karl Fischer Method)

The moisture was tested by the Japanese Pharmacopoeia General Tests moisture (coulometric titration). However, an anolyte was used Aquamicron (registered trademark) AX manufactured by Mitsubishi Chemical Corporation, and a catholyte was used Aquamicron (registered trademark) CXU. Since the water measurement by Karl Fischer method can be occurred errors within a range of ±0.3%, the value of the water content has to be understood as including values within a range of about ±0.3%.
(Measuring Method by Capillary Electrophoresis Method, CE Method)

It is a method by using Capillary Zone Electrophoresis technique and a method of separation by using free electrophoresis of each sample component in a buffer including electrolyte.

After injecting a compound solution to fused silica capillary filling a buffer adjusting the pH 2.5 to 11.5, high voltage (Inlet side +, Outlet side −) is on capillary, and then a compound moves at a speed reflecting an ionized state at the pH of the buffer (a compound having (+) charge moves quickly, and a compound having (−) charged moves slowly). pKas was calculated by plotting the difference between the migration time of the compound and that of a neutral molecule (DMSO) against pH, and fitting. Measurement condition is shown below.
Device: Beckman P/ACE system MDQ PDA
Running solution: pH 2.5 to 11.5 Buffer (10 vol % including MeOH)
Sample solution: Mixture of 10 μL of Blank DMSO and 90 μL of water 10 mM of Sample in 4 uL of DMSO stock solution, 6 uL of DMSO and 90 uL of water (Method)

Capillary: Fused silica capillary (BECKMAN COULTER, Internal diameter 50 μm, Total length 30.2 cm, Effective length 20.0 cm)

Applied voltage: 10 kV (331 V/cm)

Applied air pressure: 0.7 psi

Capillary temperature: 25° C.

Electroosmotic flow marker: DMSO

Detecting: Multiwavelength ultra violet absorption detection (Measurement wavelength; 215 nm, 238 nm)

Sample injection: Pressure method (0.5 psi, 5 sec)

As used herein, pKa is the pKa at 25° C., pKa means the pKa of the lowest value in a case of an acid having a plurality of pKa values.

Synthesis Example 1

Synthesis of the Compound (IA)

The compound (IA) was prepared according to the method described in WO2010/050468. As a result of measurement of the pKa values of the compound (IA), pKa1 was 4.2 and pKa2 was 7.2.

Example 1

Preparation of a Seed Crystal A of 2 Mole Equivalents of p-toluenesulfonic Acid Salt of the Compound (IA)

The compound (IA) (100 mg) was dissolved in 1.0 mol/L p-toluenesolufonic acid solution (2 mL) at room temperature using an ultrasonic, and the resulting solution was left to stand at 4° C., for 4 days. The precipitate was filtered to yield a seed crystal A (73 mg). It was confirmed to be a needle-like crystal by microscope.

Example 2

Preparation of a Crystalline Solid of 4-hydrates of 2 Mole Equivalents of p-toluenesulfonic Acid Salt of the Compound (IA)

The compound (IA) (2.00 g) was dissolved in p-toluenesulfonic acid monohydrate (7.58 g), acetonitrile (5 mL) and water (5 mL). Water (30 mL) was further added to the solution. To the solution was added a piece of the seed crystal A, and the resulting solution was left to stand at room temperature for three hours and at 5° C. for 16 hours. The precipitate was filtered and washed with cold water, and then dried for 45 minutes while blowing dry nitrogen gas to yield a crystalline solid (2.00 g).

Elemental analysis: (calculated as $C_{30}H_{34}ClN_7O_{10}S_2$ $2.00C_7H_8O_3S$ $4.0H_2O$)

Calculated: C, 45.22(%), H, 5.00(%), N, 8.39(%), Cl, 3.03 (%), S, 10.97(%), $H_2O$, 6.17(%)

Measured: C, 45.22(%), H, 4.91(%), N, 8.25(%), Cl, 2.86 (%), S, 11.23(%), $H_2O$ (KF method) 6.21(%)

In the X-ray powder diffraction spectrum measured by Measurement condition 1, the peaks at diffraction angle (2θ): 5.1±0.2°, 8.2±0.2°, 12.1±0.2° and 13.9±0.2° were observed.

Example 3

Preparation of a Crystalline Solid of 8.5-hydrate of 2 Mole Equivalents of p-toluenesulfonic Acid Salt of the Compound (IA)

The compound (IA) (2.00 g) was dissolved in p-toluenesulfonic acid mono-hydrate (7.58 g), acetone (5 mL) and water (5 mL). Water (30 mL) was further added to the solution. To the solution was added a piece of the seed crystal A, and the resulting solution was left to stand at room temperature for 3 hours and at 5° C. for 16 hours. The precipitate was filtered and washed with cold water, and then dried for 45 minutes while blowing dry nitrogen gas to yield a crystalline solid (2.30 g).

Elemental analysis: (calculated as $C_{30}H_{34}ClN_7O_{10}S_2$ $2.00C_7H_8O_3S$ $8.5H_2O$)

Calculated: C, 42.28(%), H, 5.40(%), N, 7.84(%), Cl, 2.84 (%), S, 10.26(%), $H_2O$, 12.25(%)

Measured: C, 42.37(%), H, 5.26(%), N, 7.79(%), Cl, 2.70 (%), S, 10.69(%), $H_2O$ (KF method) 12.11(%)

The result of the X-ray powder diffraction measured by Measurement condition 1 is shown in FIG. 1 and Table 1.

TABLE 1

| Diffraction angle 2θ (°) |
| --- |
| 5.3 |
| 8.1 |
| 8.9 |
| 10.4 |
| 10.9 |
| 13.3 |
| 17.4 |
| 19.1 |
| 20.0 |
| 21.3 |
| 24.4 |
| 25.1 |
| 26.2 |
| 27.7 |
| 29.0 |

Example 4

Preparation of a Crystalline Solid of a Mixed Acid Salt of the Compound (IA), Wherein the Mixed Salt is formed from 1 Mole Equivalent of p-toluenesuifonic Acid and 1 Mole Equivalent of Hydrochloric Acid The seed crystal A (50 mg) was dissolved in 6 mol/L HCl (0.5 mL) on an ultrasonic water bath at room temperature. After adding 1 mol/L HCl (2 mL) to the solution, the solution was left to stand at 4° C. for 2 days. The precipitated solid was filtered and washed with ice chilled water to yield a crystalline solid (23 mg). It was confirmed to be a crystalline solid by microscope.

The result of an X-ray powder diffraction measured by Measurement condition 1 is shown in FIG. 2 and Table 2.

TABLE 2

| Diffraction angle 2θ (°) |
| --- |
| 8.5 |
| 10.2 |
| 11.6 |
| 13.1 |
| 16.5 |
| 19.2 |
| 20.3 |
| 24.6 |
| 26.2 |
| 27.8 |
| 33.0 |

Example 5

Preparation of a Crystalline Solid of the Mixed Acid Salt of the Compound (IA), Wherein the Mixed Acid Salt was formed from 1 Mole Equivalent of p-toluenesulfonic Acid and 1 Mole Equivalent of Hydrobromic Acid The seed crystal A (50 mg) was dissolved in 6 mol/L HBr aqueous solution (0.25 mL) on the ultrasonic water bath at room temperature. After adding 1 mol/L HBr aqueous solution (2 mL), the solution was left to stand at 4° C. for 2 days. The precipitated solid was filtered and washed with ice chilled water to yield a crystalline solid (11 mg). It was confirmed to be a crystalline solid by microscope.
The result of the X-ray powder diffraction measured by Measurement condition 1 is shown in FIG. 3 and Table 3.

TABLE 3

| Diffraction angle 2θ (°) |
|---|
| 8.5 |
| 10.3 |
| 13.2 |
| 16.6 |
| 19.3 |
| 20.3 |
| 22.0 |
| 24.7 |

TABLE 3-continued

| Diffraction angle 2θ (°) |
|---|
| 26.3 |
| 27.8 |
| 29.6 |
| 33.0 |

Example 6

Preparation of the Type I Crystal: a Crystalline Solid of Hydrate of a Mixed Acid Salt of the Compound (IA), Wherein the Mixed Acid Salt was formed from 1.3 Mole Equivalents of p-toluenesulfonic Acid and 0.35 Mole Equivalents of Sulfuric Acid

Example 6-1

Synthesis of the Type I Crystal D
Step 1: Preparation of a Seed Crystal C
The seed crystal A (50 mg) was dissolved in 6 mol/L $H_2SO_4$ (3 mL) on an ultrasonic water bath at room temperature, and the solution was left to stand at 4° C. for 2 days. The precipitated crystalline solid was filtered and washed with ice chilled water to yield a seed crystal C (23 mg).
Step 2: Synthesis of the Compound (IA) and Preparation of the Type I Crystal D

[Chemical formula 7]

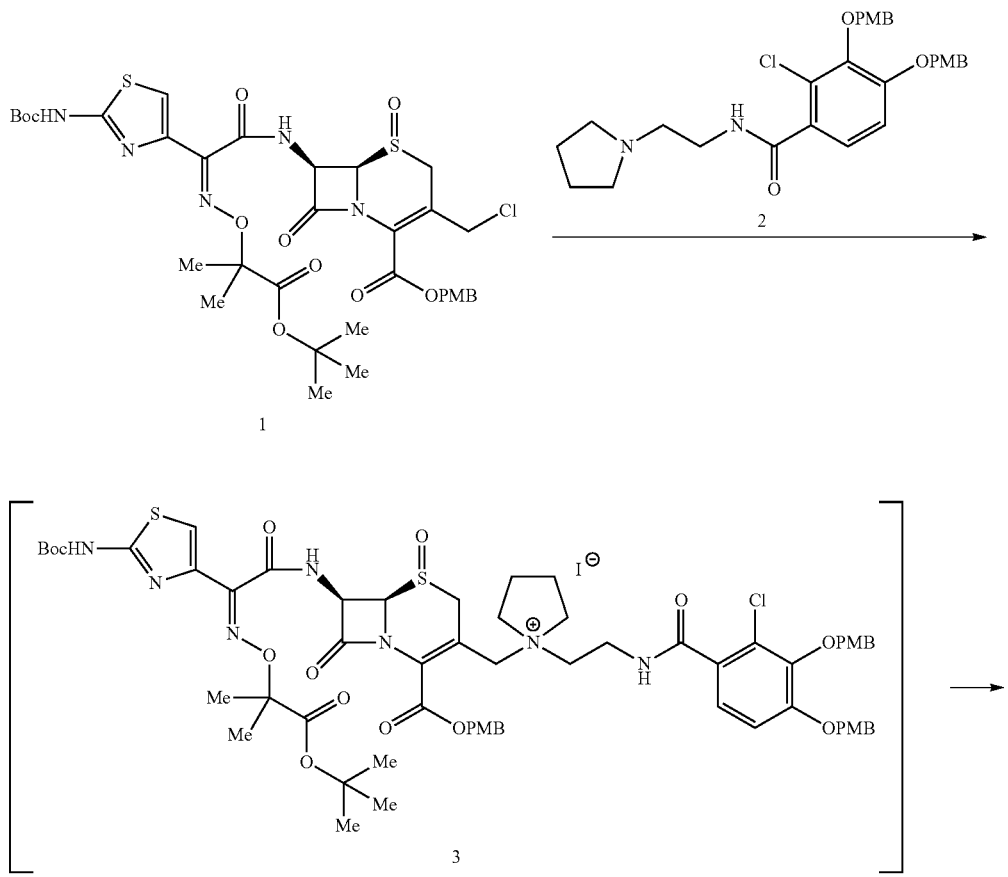

-continued

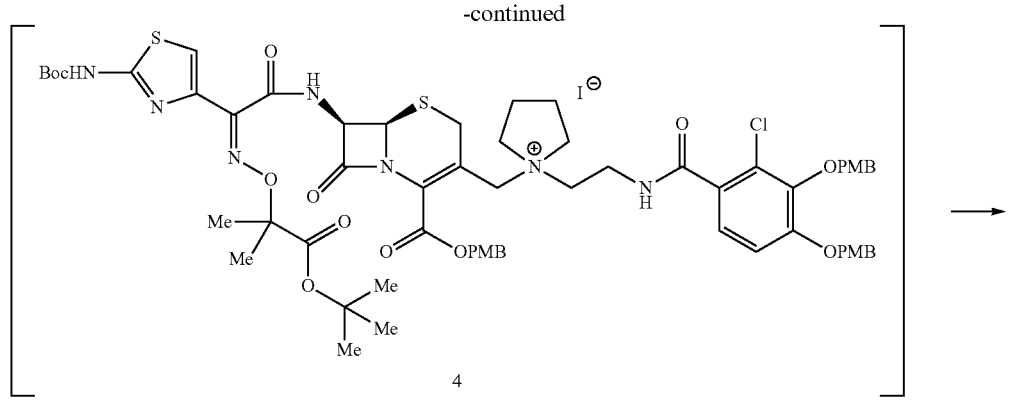

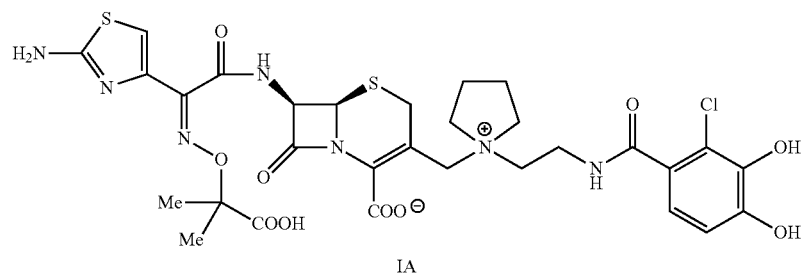

Under a nitrogen atmosphere, the compound 1 (18.0 kg, 22.6 mol) was dissolved in N, N-dimethylacetoamide (41 L), and cooled to 0° C. Sodium iodide (6.8 kg, 45.2 mol), the compound 2 (13.1 kg, 24.9 mol), and N,N-dimethylacetoamide (4 L) are added to the solution at 0° C. for 6 days. The solution was warmed to 7° C., and stirred for 16 hours. The solution was cooled to 0° C. and sodium iodide (5.1 kg, 33.9 mol) was added to the solution, and then acetyl chloride (8.9 kg, 113.0 mol) was dropped over 90 minutes at 0° C., the solution was stirred at 0° C. for 5 hours.

Anisole (36 L) was added to the reaction solution, this solution was added to the mixed solution of methyl ethyl ketone and aqueous solution of sodium bisulfite, and extracted. The organic layer was washed with the mixed solution of sulfuric acid and brine twice.

Anisole (90 L) was added and the solution was cooled to 15° C. 75% sulfuric acid (36.0 kg) was added to the solution, it was stirred at 28° C. for 2 hours. After adding water (90 L) and ethyl acetate (36 L), the resulting solution was extracted. The obtained aqueous layer was washed with ethyl acetate twice, and then purified by reverse phase column chromatography (acetonitrile-sulfuric acid aqueous solution) using a chromatographic separation small particle size synthetic adsorbent (Diaion™ HP20SS). After adding an aqueous solution of 75% sulfuric acid (33.4 kg) and p-toluenesulfonic acid monohydrate (16.7 kg), it was added an appropriate amount of the seed crystal C to precipitate a solid. It was cooled to 5° C. and stirred at 5° C. for 10 hours, and the precipitated crystalline solid was filtered. The crystalline solid was washed with water cooled to 5° C., and then dried under reduced pressure at about 33 hPa for about 3 hours to yield a type I crystal D of the compound (IA) (12.7 kg, content conversion yield: 49%).

The contents of p-toluenesulfonic acid and sulfuric acid in the type I crystal D were determined by the following method.

(p-Toluenesulfonic Acid Content Measuring Method)

Step 1: Preparation of a Sample Solution

About 40 mg of the sample was weighed precisely, and dissolved in a sample dilution solvent to be exactly 25 mL. To 2 mL of this solution weighed precisely was added a sample dilution solvent to be prepared exactly 20 mL solution.

Step 2: Preparation of a Standard Solution

About 25 mg of a standard preparation of sodium p-toluenesulfonate equilibrated humidity under the condition of 25° C./60% RH was weighed precisely, and dissolved in a sample dilution solvent to be exactly 100 mL. To 5 mL of this solution weighed precisely was added a sample dilution solvent to be prepared exactly 50 mL solution.

5 mmol/L phosphate buffer/liquid chromatography acetonitrile mixture (9:1) was used as the above sample dilution solvent. Herein, water: 0.05 mol/L sodium dihydrogen phosphate test solution: 0.05 mol/L disodium hydrogen phosphate reagent mixture=18:1:1 (pH is about 7.1) was used as a phosphate buffer.

Step 3: Measurement and Determination

The peak area of p-toluenesulfonic acid was determined in an automatic integration method by measuring the above sample solution and the standard solution in the following test condition by liquid chromatography. Note that an anhydrous basis (a dehydration product conversion) is calculated values omitted the water content from the total amount as 100%.

(Test Condition)
Column: Unison UK-C18, φ4.6×150 mm, 3 µm, by Imtakt
Column temperature: constant temperature at near 35° C.
Flow rate: 1.0 mL per minute (a retention time of p-toluenesulfonic acid: about 7 minutes)
Detector: ultraviolet absorption spectrophotometer (wavelength: 218 nm)
Mobile phase A: 0.1% trifluoroacetic acid solution
Mobile phase B: acetonitrile for liquid chromatography
Gradient program

| Time after addition (minute) | Mobile phase A (vol %) | Mobile phase B (vol %) |
|---|---|---|
| 0~7 | 95 | 5 |
| 7~7.01 | 95→60 | 5→40 |
| 7.01~15 | 60 | 40 |
| 15~15.01 | 60→95 | 40→5 |
| 15.01~25 | 95 | 5 |

The content of p-toluenesulfonic acid in the sample was determined using the following formula.

$$\text{The amount of } p\text{-toluenesulfonic acid } (\%) = \frac{M_S}{M_T} \times \frac{P}{100} \times \frac{100}{100-W_T} \times \frac{A_T}{A_S} \times \frac{172.20}{194.18} \times \frac{1}{4} \times 100$$

$M_S$: weighed amount of a standard preparation of sodium p-toluenesulfonate (mg)
$M_T$: weighed amount of a sample (mg)
P: purity of a standard preparation of sodium p-toluenesulfonate (%)
$W_T$: water of a sample (%)
$A_T$: peak area of p-toluenesulfonic acid obtained from the sample solution
$A_S$: peak area of p-toluenesulfonic acid obtained from the standard solution
172.20: molecular weight of p-toluenesulfonic acid
194.18: molecular weight of sodium p-toluenesulfonate
1/4: dilution rate
(Sulfuric Acid Content Measuring Method)
Step 1: Preparation of a Standard Solution
About 50 mg of sodium sulfate anhydrous was weighed precisely, and dissolved in a mobile phase to be exactly 25 mL. To 2 mL of this liquid weighed precisely was added a mobile phase to be exactly 50 mL. Furthermore, to 2 mL of this liquid weighed precisely was added a mobile phase to be exactly 20 mL.
Step 2: Preparation of a Sample Solution
About 30 mg of a sample was weighed precisely, and dissolved in a mobile phase to be exactly 25 mL. To 2 mL of this liquid weighed precisely was added a mobile phase to be exactly 20 mL.
Step 3: Measurement and Determination
The peak area of sulfate ion was determined in an automatic integration method by measuring the above sample solution and the standard solution in the following test condition by liquid chromatography.

(Test Condition)
Column: Shim-pack IC-A3, φ4.6×150 mm, 5 µm, Shimadzu Corporation
Column temperature: constant temperature at near 40° C.
Flow rate: 1.2 mL per minute (a retention time of sulfate ion: about 15 minutes)
Detector: electric conductivity detector (non-suppressor system)
Mobile phase: the solution obtained by the following: about 0.67 g of Bis-Tris, about 3.09 g of boric acid, and about 1.11 g of the ground p-hydroxybenzoic acid weighed precisely were dissolved in water to be exactly 1000 mL.
The content of sulfuric acid in the sample was determined using the following formula.

$$\text{The amount of sulfuric acid } (\%) = M_S/M_T \times 100/(100-W_T) \times A_T/A_S \times 98.08/142.04 \times 1/25 \times 100$$

$M_S$: weighed amount of sodium sulfate anhydrous (mg)
$M_T$: weighed amount of a sample (mg)
$W_T$: water of a sample (%)
$A_S$: peak area of sulfate ion obtained from the standard solution
$A_T$: peak area of sulfate ion obtained from the sample solution
98.08: molecular weight of sulfuric acid
142.04: molecular weight of sodium sulfate anhydrous
1/25: dilution rate
(Result)
p-Toluenesulfonic acid: 22.2±0.2% (on an anhydrous basis)
Sulfuric acid: 4.3±0.1% (on an anhydrous basis)
Elemental analysis: (calculated as $C_{30}H_{34}N_7ClO_{10}S_2$ $1.32C_7H_8O_3S$ $0.45H_2SO_4$ $9.0H_2O$)
Calculated: C, 39.75(%), H, 5.39(%), N, 8.27(%), Cl, 2.99(%), S, 10.19(%), $H_2O$, 13.67(%)
Measured: C, 39.73(%), H, 5.33(%), N, 8.53(%), Cl, 3.08(%), S, 10.11(%), $H_2O$ (KF method) 13.69(%)
The result of the X-ray powder diffraction measured by Measurement condition 2 is shown in FIG. 4 and Table 4. It should be noted that an aluminium plate as a sample folder. The peak whose 2-theta (2θ) value is around 38° is the peak of aluminium.

TABLE 4

| Diffraction angle 2θ (°) |
|---|
| 8.3 |
| 9.0 |
| 10.1 |
| 11.5 |
| 13.0 |
| 16.3 |
| 17.3 |
| 18.1 |
| 19.1 |
| 19.9 |
| 20.3 |
| 20.8 |
| 21.6 |
| 26.2 |

The diffraction angles (2θ) showing characteristic diffraction peaks are 8.3±0.2°, 9.0±0.2°, 10.1±0.2°, 13.0±0.2°, 16.3±0.2°, 17.3±0.2°, 18.1±0.2°, 19.1±0.2°, 20.3±0.2° and 26.2±0.2°. Preferable is 8.3±0.2°, 10.1±0.2°, 13.0±0.2°, 16.3±0.2° and 20.3±0.2°. Further preferable is 8.3±0.2°, 10.1±0.2°, 13.0±0.2° and 20.3±0.2°.

(Example 6-2) Synthesis of the Type I Crystal E

The type I crystal D (25.0 g) obtained by the method described in Example 6-1 was suspended in water cooled to 5° C. (125 mL) and stirred for 26 hours at 5° C., and the precipitated crystalline solid was filtered. The crystalline solid was washed with water cooled to 5° C. (75 mL) to yield a type I crystal E of the compound (IA) (22.92 g).

The contents of p-toluenesulfonic acid and sulfuric acid in the type I crystal E were determined by the method described in the above Example 6-1.

(Result)
p-Toluenesulfonic acid: 21.9±0.2% (on an anhydrous basis)
Sulfuric acid: 3.9±0.1% (on an anhydrous basis)
Elemental analysis: (calculated as $C_{30}H_{34}N_7ClO_{10}S_2$ $1.30O_7H_8O_3S$ $0.35H_2SO_4$ $9.0H_2O$)
Calculated: C, 40.05(%), H, 5.42(%), N, 8.36(%), Cl, 3.02(%), S, 9.98(%), $H_2O$, 13.82(%)
Measured: C, 39.96(%), H, 5.32(%), N, 8.59(%), Cl, 2.99 (%), S, 10.11(%), $H_2O$ (KF method) 13.78(%).

The result of the X-ray powder diffraction measured by Measurement condition 2 is shown in FIG. 5 and Table 5. It should be noted that an aluminium plate as a sample folder. The peak whose 2-theta (2θ) value is around 38° is the peak of aluminium.

TABLE 5

| Diffraction angle 2θ (°) |
|---|
| 8.3 |
| 9.0 |
| 10.1 |
| 11.5 |
| 13.0 |
| 16.3 |
| 17.3 |
| 18.1 |
| 19.1 |
| 19.9 |
| 20.3 |
| 20.8 |
| 21.6 |
| 26.2 |

The diffraction angles (2θ) showing characteristic diffraction peaks are, 8.3±0.2°, 9.0±0.2°, 10.1±0.2°, 13.0±0.2°, 16.3±0.2°, 17.3±0.2°, 18.1±0.2°, 19.1±0.2°, 20.3±0.2° and 26.2±0.2°. Preferable is 8.3±0.2°, 10.1±0.2°, 13.0±0.2°, 16.3±0.2° and 20.3±0.2°. Further preferable is 8.3±0.2°, 10.1±0.2°, 13.0±0.2° and 20.3±0.2°.

As described above, although there is a difference of the content of p-toluenesulfonic acid and sulfuric acid between the type I crystal D and the type I crystal E, they are same crystalline form since they have the same X-ray powder diffraction pattern. That is, the type I crystal D is a crystalline solid remaining about 0.02 mole equivalents of p-toluenesulfonic acid and about 0.1 mole equivalent of sulfuric acid with the type I crystal E.

The type I crystal may contain remaining about 0.01 to 0.1 mole equivalents of p-toluenesulfonic acid and/or about 0.01 to 0.1 mole equivalents of sulfuric acid. The remaining acid may be in the form adhered to a crystal or the form incorporated into a crystal.

The preferable content of p-toluenesulfonic acid of the type I crystal is about 20.2±0.2 to 23.2±0.2% (on an anhydrous basis), the preferable content of sulfuric acid is about 3.5±0.1 to 5.0±0.1% (on an anhydrous basis). The more preferable content of p-toluenesulfonic acid is about 21.5±0.2 to 22.3±0.2% (on an anhydrous basis), the more preferable content of sulfuric acid is about 4.2±0.1 to 4.9±0.1% (on an anhydrous basis). The further preferable content of p-toluenesulfonic acid of the type I crystal is about 21.5 to 22.3% (on an anhydrous basis), further preferable content of sulfuric acid is about 4.2 to 4.9% (on an anhydrous basis).

Example 7

Preparation of a Crystalline Solid of 2 Mole Equivalents of Benzenesulfonic Acid Salt of the Compound (IA)

The betaine of the compound (IA) (100 mg) was dissolved in 1.0 mol/L benzenesulfonate aqueous solution (5.5 mL) at room temperature using ultrasonic. To the solution was added a piece of the seed crystal A, the solution was left to stand at 5° C. for 4 days. The precipitate was filtered to obtain a seed crystal B (27 mg).

The betaine of the compound (IA) (300 mg) was dissolved in acetonitrile (0.30 mL) and water (0.75 mL), and benzenesulfonic acid (949 mg) was added to the solution. After further adding water (3.0 mL) to the solution, a piece of seed crystal B was added to the solution, and the solution was left to stand at 5° C. for 5 days. The precipitate was filtered to yield a crystalline solid (79.8 mg).

The results of the X-ray powder diffraction measured by Measurement condition 1 were shown in FIG. 6 and Table 6.

TABLE 6

| Diffraction angle 2θ (°) |
|---|
| 8.4 |
| 9.2 |
| 10.3 |
| 11.6 |
| 13.3 |
| 16.5 |
| 19.2 |
| 19.6 |
| 20.3 |
| 20.8 |
| 22.1 |
| 23.6 |
| 24.5 |
| 25.2 |
| 26.3 |
| 31.2 |
| 32.4 |
| 33.1 |
| 34.3 |

Example 8

Measurement of Dynamic Vapor Sorption of the Type I Crystal D and X-Ray Powder Diffraction in Each Humidity The results of a dynamic vapor sorption measurement of the type I crystal D obtained in Example 6-1 were shown in FIG. 7 and Table 7. Dynamic vapor sorption measurement can be occurred errors within the range of ±0.5%. An increased amount of water (%) represents an increased amount of the type I crystal at 0% RH.

TABLE 7

| Relative humidity (% RH) | Increased amount of water (%) |
|---|---|
| 0 | 0.00 |
| 5 | 3.33 |
| 10 | 5.26 |
| 15 | 7.70 |
| 20 | 10.53 |
| 25 | 11.67 |
| 30 | 12.28 |
| 35 | 12.75 |
| 40 | 13.16 |
| 45 | 13.54 |
| 50 | 13.91 |
| 55 | 14.25 |
| 60 | 14.55 |
| 65 | 14.93 |
| 70 | 15.26 |
| 75 | 15.55 |
| 80 | 15.82 |
| 85 | 16.08 |
| 90 | 16.34 |
| 95 | 16.60 |

The results of X-ray powder diffraction measured by Measurement condition 3 using the type I crystal D which is held for 3 hours or more at each relative humidity conditions were shown below.

The result of X-ray powder diffraction at 30% RH conditions is shown in FIG. 8 and Table 8.

TABLE 8

| Diffraction angle 2θ (°) |
|---|
| 8.4 |
| 9.1 |
| 10.2 |
| 11.6 |
| 13.0 |
| 16.4 |
| 17.4 |
| 18.2 |
| 19.2 |
| 20.1 |
| 20.4 |
| 26.2 |
| 27.8 |

The diffraction angels (2θ) showing characteristic diffraction peaks are 8.4±0.2°, 9.1±0.2°, 10.2±0.2°, 11.6±0.2°, 13.0±0.2°, 20.1±0.2°, 20.4±0.2° and 26.2±0.2°. Preferable is 8.4±0.2°, 10.2±0.2°, 13.0±0.2° and 20.4±0.2°.

The result of the X-ray powder diffraction at 40% RH conditions is shown in FIG. 9 and Table 9.

TABLE 9

| Diffraction angle 2θ (°) |
|---|
| 8.4 |
| 9.1 |
| 10.2 |
| 11.5 |
| 13.0 |
| 16.4 |
| 17.4 |
| 18.2 |
| 19.2 |
| 20.0 |
| 20.3 |
| 20.8 |
| 21.7 |
| 22.0 |
| 23.9 |
| 24.6 |
| 25.3 |
| 26.2 |
| 27.8 |
| 31.9 |
| 33.0 |

The diffraction angels (2θ) showing characteristic diffraction peaks are 8.4±0.2°, 9.1±0.2°, 10.2±0.2°, 11.5±0.2°, 13.0±0.2°, 20.0±0.2°, 20.3±0.2°, 21.7±0.2° and 26.2±0.2°. Preferable is 8.4±0.2°, 10.2±0.2°, 13.0±0.2° and 20.3±0.2°.

The result of X-ray powder diffraction at 50% RH conditions is shown in FIG. 10 and Table 10.

TABLE 10

| Diffraction angle 2θ (°) |
|---|
| 8.4 |
| 9.1 |
| 10.2 |
| 11.5 |
| 13.0 |
| 14.2 |
| 14.7 |
| 16.4 |
| 17.3 |
| 18.2 |
| 19.2 |
| 20.0 |
| 20.3 |
| 20.8 |
| 21.7 |
| 22.0 |
| 24.0 |
| 24.6 |
| 25.2 |
| 25.7 |
| 26.2 |
| 27.8 |

The diffraction angles (2θ) showing characteristic diffraction peaks are 8.4±0.2°, 9.1±0.2°, 10.2±0.2°, 11.5±0.2°, 13.0±0.2°, 20.0±0.2°, 20.3±0.2°, 21.7±0.2° and 26.2±0.2°. Preferable is 8.4±0.2°, 10.2±0.2°, 13.0±0.2° and 20.3±0.2°.

The result of X-ray powder diffraction at 60% RH conditions is shown in FIG. 11 and Table 11.

TABLE 11

| Diffraction angle 2θ (°) |
|---|
| 8.3 |
| 9.1 |
| 10.0 |
| 10.2 |
| 11.5 |
| 13.0 |
| 14.2 |

TABLE 11-continued

| Diffraction angle 2θ (°) |
| --- |
| 16.3 |
| 17.3 |
| 18.1 |
| 19.1 |
| 19.9 |
| 20.3 |
| 20.5 |
| 20.8 |
| 21.6 |
| 22.1 |
| 23.5 |
| 23.8 |
| 24.3 |
| 24.6 |
| 25.1 |
| 26.2 |
| 28.3 |
| 28.9 |
| 29.4 |
| 31.3 |
| 32.1 |
| 33.1 |

The diffraction angles (2θ) showing characteristic diffraction peaks are 8.3±0.2°, 9.1±0.2°, 10.2±0.2°, 11.5±0.2°, 13.0±0.2°, 19.9±0.2°, 20.3±0.2°, 6±0.2° and 26.2±0.2°. Preferable is 8.3±0.2°, 10.2±0.2°, 13.0±0.2° and 20.3±0.2°.

The result of X-ray powder diffraction at 70% RH conditions is shown in FIG. 12 and Table 12.

TABLE 12

| Diffraction angle 2θ (°) |
| --- |
| 8.3 |
| 9.0 |
| 9.9 |
| 10.1 |
| 11.5 |
| 13.0 |
| 14.1 |
| 16.1 |
| 16.5 |
| 17.2 |
| 18.1 |
| 19.1 |
| 19.9 |
| 20.3 |
| 20.6 |
| 20.8 |
| 21.6 |
| 22.1 |
| 23.3 |
| 24.2 |
| 24.5 |
| 25.0 |
| 25.5 |
| 26.2 |
| 28.2 |
| 28.8 |
| 29.4 |
| 31.3 |
| 32.2 |
| 33.2 |

The diffraction angles (2θ) showing characteristic diffraction peaks are 8.3±0.2°, 0±0.2°, 1±0.2°, 11.5±0.2°, 13.0±0.2°, 19.9±0.2°, 20.3±0.2°, 21.6±0.2° and 26.2±0.2°. Preferable is 3±0.2°, 10.1±0.2°, 13.0±0.2° and 20.3±0.2°.

The result of X-ray powder diffraction at 80% RH conditions is shown in FIG. 13 and Table 13.

TABLE 13

| Diffraction angle 2θ (°) |
| --- |
| 8.3 |
| 9.0 |
| 9.7 |
| 10.1 |
| 11.5 |
| 13.0 |
| 14.0 |
| 16.2 |
| 16.5 |
| 17.1 |
| 18.0 |
| 19.1 |
| 19.3 |
| 19.9 |
| 20.3 |
| 20.7 |
| 21.6 |
| 22.2 |
| 23.1 |
| 23.4 |
| 24.1 |
| 24.4 |
| 24.9 |
| 26.2 |
| 28.2 |
| 28.7 |
| 29.3 |
| 32.3 |

The diffraction angles (2θ) showing characteristic diffraction peaks are 8.3±0.2°, 0±0.2°, 10.1±0.2°, 11.5±0.2°, 13.0±0.2°, 19.9±0.2°, 20.3±0.2°, 21.6±0.2° and 26.2±0.2°. Preferable is 8.3±0.2°, 10.1±0.2°, 13.0±0.2° and 20.3±0.2°.

The result of the X-ray powder diffraction at 90% RH conditions is shown in FIG. 14 and Table 14.

TABLE 14

| Diffraction angle 2θ (°) |
| --- |
| 8.3 |
| 9.0 |
| 9.6 |
| 10.1 |
| 11.5 |
| 13.1 |
| 14.0 |
| 15.6 |
| 16.1 |
| 16.5 |
| 17.1 |
| 17.9 |
| 18.7 |
| 19.0 |
| 19.4 |
| 19.9 |
| 20.3 |
| 20.8 |
| 21.6 |

TABLE 14-continued

| Diffraction angle 2θ (°) |
|---|
| 22.3 |
| 22.9 |
| 23.2 |
| 23.7 |
| 24.3 |
| 24.8 |
| 26.2 |
| 28.1 |
| 28.8 |
| 29.2 |
| 30.3 |
| 32.4 |

The diffraction angles (2θ) showing characteristic diffraction peaks are 8.3±0.2°, 9.0±0.2°, 10.1±0.2°, 11.5±0.2°, 13.1±0.2°, 19.9±0.2°, 20.3±0.2°, 21.6±0.2° and 26.2±0.2°. Preferable is 8.3±0.2°, 10.1±0.2°, 13.1±0.2° and 20.3±0.2°.

The result of the X-ray powder diffraction at 95% RH conditions is shown in FIG. 15 and Table 15.

TABLE 15

| Diffraction angle 2θ (°) |
|---|
| 8.2 |
| 9.0 |
| 9.6 |
| 10.1 |
| 11.5 |
| 13.0 |
| 14.0 |
| 15.6 |
| 16.0 |
| 16.6 |
| 17.1 |
| 17.9 |
| 18.6 |
| 19.0 |
| 19.4 |
| 19.9 |
| 20.3 |
| 20.8 |
| 21.5 |
| 22.3 |
| 22.8 |
| 23.1 |

TABLE 15-continued

| Diffraction angle 2θ (°) |
|---|
| 24.2 |
| 24.7 |
| 26.2 |
| 28.1 |
| 28.8 |
| 29.3 |
| 32.5 |

The diffraction angles (2θ) showing characteristic diffraction peaks are 8.2±0.2°, 9.0±0.2°, 10.1±0.2°, 11.5±0.2°, 13.0±0.2°, 19.9±0.2°, 20.3±0.2°, 5±0.2° and 26.2±0.2°. Preferable is 8.2±0.2°, 10.1±0.2°, 13.0±0.2° and 20.3±0.2°.

From the above results, it is suggested that the type I crystal can come into being adsorption of moisture by change of relative humidity to make hydration water, and the most hydration water is incorporated in the crystal lattice as crystal water. In other words, the type I crystal is the crystalline solid that water molecules can easily move in and out through the crystal lattice as crystal water depending on an external humidity change. That is, as shown in FIGS. 7 to 15, the type I crystal is a crystalline solid wherein the number of its hydration water can change at the degree to hold several hours under different humidity environment, and these type I crystals can be substantially interpreted as the same crystalline solid even if they are different in the number of hydration water, that is different composition in the content of water. The hydration water may be crystal water, adhere water, or residual solvent.

A preferred content of water of the type I crystal is about 12 to 17%, more preferable is about 12 to 15%. A preferred hydration water of the type I crystal is about 7 to 12 mole, more preferable is about 8 to 11.5 mole.

These type I crystals having different content of water have characteristic diffraction peaks in common. The diffraction angels (2θ) showing characteristic diffraction peaks are 8.2±0.2°, 8.9±0.2°, 10.1±0.2°, 11.4±0.2°, 13.0±0.2°, 19.9±0.2°, 20.3±0.2°, 21.5±0.2° and 26.2±0.2°. Preferable is 8.2±0.2°, 8.9±0.2°, 10.1±0.2°, 11.4±0.2°, 13.0±0.2°, 19.9±0.2°, 20.3±0.2° and 26.2±0.2°. More preferable is 8.2±0.2°, 10.1±0.2°, 13.0±0.2° and 20.3±0.2°.

Example 9

Preparation of Sodium Salt of the Compound (IA)

[Chemical formula 8]

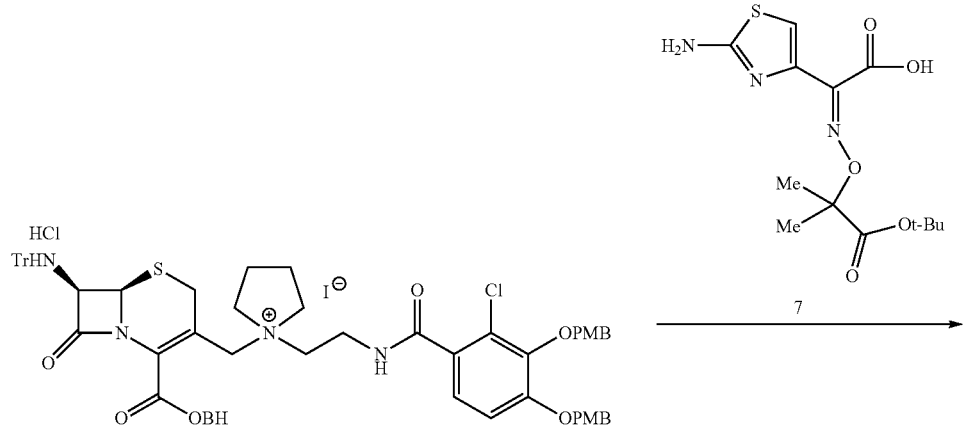

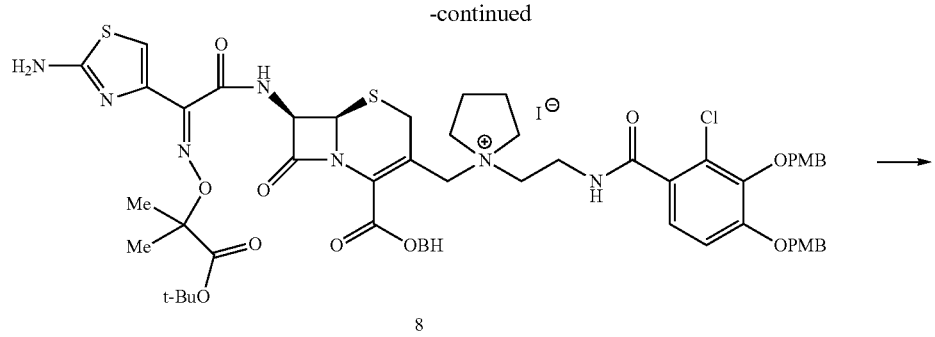

8

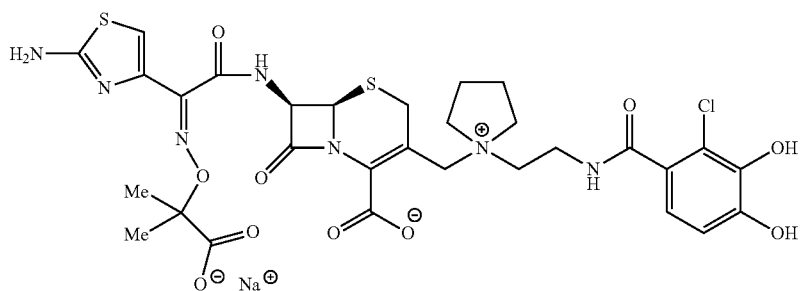

9

Step 1 Synthesis of the Compound 8

The compound 6 (970 g, 713 mmol, 78 w/w % purity) was dissolved in dichloromethane (7.13 L), the compound 7 was added at 15° C. as internal temperature to the solution. The suspension was cooled to −25° C., and EDC hydrochloride (150.35 g, 784 mmol) and pyridine (46 mL, 570 mmol) were added, and then the reaction solution was stirred at −20° C. for 3 hours. The reaction solution was added to the mixed solution of 2 mol/L hydrochloric acid (285 mL), cold-water (7.2 L), and ethyl acetate (2.4 L), the dichloromethane was distilled off under reduced pressure. To the obtained solution was added ethyl acetate (4.5 L), the resulting solution was washed with brine twice. The organic layer was concentrated under reduced pressure to yield a crude product containing the compound 8 (1250 g). The crude product containing the compound 8 was used in the next step without purification.

Step 2 Synthesis of the Compound 8

To anisole (1.54 L) cooling in dry ice-ethanol bath was added aluminium chloride (495.4 g, 3.71 mol) followed by dichloromethane. 610 g of the crude product containing the compound 8 obtained by Step 1 was dissolved in a mixed solution of dichloromethane (0.51 L) and anisole (1.03 L) and spent 1 hour adding dropwise to the above aluminium chloride solution re-cooling to −40° C. The container used for the dropwise was washed with a mixed solution of dichloromethane (0.36 L) and anisole (0.51 L) and the wash fluid was added to the reaction solution. The reaction solution was stirred at −20° C. for 2 hours, and added to a mixed solution of ethanol (7.1 L), 1 mol/L hydrochloric acid (7.1 L) while stirring under cooling in ice-bath. The mixed solution was stirred for 30 minutes under ice-cooling, dichloromethane (5.14 L) and saturated brine (257 mL) was added, the separated aqueous layer was washed with dichloromethane (5.14 L). The organic layer was extracted with a mixture of water (2.57 L) and saturated brine (100 mL), and the separated aqueous layer was combined with the previous aqueous layer. The aqueous layer was stirred under cooling in ice-bath, and 2 mol/L sodium hydroxide aqueous solution was added to adjust pH to 1.5 and the solution was left to stand. The aqueous layer was concentrated and purified by HP20SS column (eluent: 13% acetonitrile water). Sodium bicarbonate (8.75 g) was added to the collected fractions containing the target product and the resulting solution was concentrated under reduced pressure until 500 mL. The solution was diluted by adding water (1.6 L) and filtered with cotton plug, and then the filtrate was lyophilized to yield the compound 9 (77.8 g).

Elemental analysis: (calculated as $C_{30}H_{33}ClN_7O_{10}S_2Na$ $4.5H_2O$)

Calculated: C; 42.13, H; 4.95, N; 11.46, S; 7.50, Cl; 4.14, Na; 2.69(%)

Measured: C; 42.22, H; 4.88, N; 11.24, S; 7.01, Cl; 4.04, Na; 2.74(%)

The solubility of the obtained compound 9 in various aqueous medium (water for injection, saline, dextrose solution) was all 100 mg/mL or more, and they are very high solubility.

Example 10

Preparation of a Crystalline Solid of a Mixed Acid Salt of the Compound (IA), Wherein the Mixed Acid is formed from 1 Mole Equivalent of p-toluenesulfonic Acid and 1 Mole Equivalent of Nitric Acid A seed crystal A (20 mg) obtained in the same manner as in Example 1 was dissolved in 2 mol/L HNO3 aqueous solution (0.3 mL). The solution was left to stand at 4° C. for 2 days. The precipitated solid was collected to yield a crystalline solid. It was confirmed to be a crystalline solid by using the microscope.

The result of X-ray powder diffraction measured by Measurement condition 1 is shown in Table 1.

TABLE 16

| Diffraction angle 2θ (°) |
| --- |
| 8.5 |
| 9.4 |
| 10.6 |
| 20.0 |
| 20.4 |
| 24.9 |

Example 11

Preparation of a Crystalline Solid of a Mixed Acid Salt of the Compound (IA), Wherein the Mixed Acid Salt is formed from 1.05 Mole Equivalents of p-toluenesulfonic Acid and 0.65 Mole Equivalents of Sulfuric Acid Preparation of a Crystalline Solid of 9 Hydrates of a Mixed Acid Salt of the Compound (IA), Wherein the Mixed Acid Salt is formed from 1.05 Mole Equivalents of p-toluenesulfonic Acid and 0.65 Mole Equivalents of Sulfuric Acid The type I crystal D (2.00 g) obtained by the method according to Example 6-1 was dissolved in 50% acetonitrile aqueous solution (10 mL), water (40 mL) and 75% sulfuric acid (4.0 g) was added, the solution was stirred at 15° C. for 5 hours 20 minutes. The solution was cooled to 0° C., stirred for 1 hour 10 minutes, and left to stand for 14 hours 10 minutes in a refrigerator. The precipitated crystal was filtered, washed with cold water (6 mL), and air-dried to yield a crystalline solid (1.74 g).

The obtained crystalline solid (1.5 g) was dissolved in 50% acetonitrile aqueous solution (7.5 mL), water (30 mL) and 75% sulfuric acid (3.0 g) were added, and the solution was stirred at 15° C. for 3 hours 30 minutes. The solution was cooled to 0° C. and stirred for 3 hours, and then left to stand for 14 hours 50 minutes at a refrigerator. The precipitated crystalline solid was filtered, washed with cold water (4.5 mL) and air-dried to yield a crystalline solid (1.17 g).

The water content measurement was measured by the Karl Fischer method. The content of p-toluenesulfonic acid and sulfuric acid were measured in the same manner as described in Example 6-1.

(Result)
Water content: 14.0±0.3%
p-Toluenesulfonic acid: 18.2±0.2% (on an anhydrous basis)
Sulfuric acid: 6.4±0.1% (on an anhydrous basis)
According to the above results, the crystalline solid is $C_{30}H_{34}N_7ClO_{10}S_2$ $1.05C_7H_8O_3S$ $0.65H_2SO_4$ $9.0H_2O$.

The result of the X-ray powder diffraction measured by Measurement condition 1 is shown in FIG. 16 and Table 17.

TABLE 17

| Diffraction angle 2θ (°) |
| --- |
| 8.4 |
| 9.1 |
| 10.2 |
| 11.6 |
| 13.1 |
| 14.2 |
| 16.3 |
| 17.3 |
| 19.2 |
| 20.1 |
| 20.4 |
| 21.7 |
| 26.3 |

The diffraction angles (2θ) showing characteristic diffraction peaks are 8.4±0.2°, 9.1±0.2°, 10.2±0.2°, 13.1±0.2°, 16.3±0.2°, 17.3±0.2°, 19.2±0.2°, 20.4±0.2° and 26.3±0.2°. Preferable is 8.4±0.2°, 10.2±0.2°, 13.1±0.2°, 16.3±0.2° and 20.4±0.2°. Further preferable is 8.4±0.2°, 10.2±0.2°, 13.1±0.2° and 20.4±0.2°.

Example 12

A Crystalline Solid of Hydrate of a Mixed Acid Salt of the Compound (IA), Wherein the Mixed Acid Salt is formed from 1.0 Mole Equivalent of p-toluenesulfonic Acid and 0.5 Mole Equivalents of Sulfuric Acid The type I crystal D (50.0 g) obtained by the method described in Example 6-1 was dissolved in a mixture of ethanol (300 mL) and water (200 mL). A mixed solution of 75% sulfuric acid (100 g) and water (500 mL) was added at room temperature, and then water (400 mL) was further added. The solution was cooled to 0° C. and stirred for 6 hours to precipitate a crystal, and the precipitated crystalline solid was filtered. The crystal was washed with water cooled to 5° C. (600 mL) to yield a crystalline solid (26.8 g).

The contents of p-toluenesulfonic acid and sulfuric acid of the obtained crystalline solid were quantified by the method described in Example 6-1.

(Result)
p-Toluenesulfonic acid: 18.3±0.2% (on an anhydrous basis)
Sulfuric acid: 4.9±0.1% (on an anhydrous basis)
Elemental analysis: (calculated as $C_{30}H_{34}N_7ClO_{10}S_2$ $1.0C_7H_8O_3S$ $0.5H_2SO_4$ $10.0H_2O$)
Calculated: C, 38.52(%), H, 5.50(%), N, 8.50(%), Cl, 3.07 (%), S, 9.73(%), $H_2O$, 15.61(%)
Measured: C, 38.69(%), H, 5.31(%), N, 8.67(%), Cl, 3.04 (%), S, 9.84(%), $H_2O$ (KF method) 15.85(%).

The result of the X-ray powder diffraction measured by Measurement condition 2 is shown in FIG. 17 and Table 18. It should be noted that the aluminium plate is used as a sample folder. The peak whose 2-theta (2θ) value is around 38° is the peak of aluminium.

TABLE 18

| Diffraction angle 2θ (°) |
| --- |
| 8.3 |
| 9.0 |
| 10.1 |
| 11.5 |
| 13.0 |
| 16.5 |
| 17.2 |
| 18.1 |
| 19.1 |
| 20.0 |
| 20.3 |
| 20.9 |
| 21.7 |
| 26.3 |

The diffraction angles (2θ) showing characteristic diffraction peaks are 8.3±0.2°, 9.0±0.2°, 10.1±0.2°, 13.0±0.2°, 16.5±0.2°, 17.2±0.2°, 18.1±0.2°, 19.1±0.2°, 20.3±0.2° and 26.3±0.2°. Preferable is 8.3±0.2°, 10.1±0.2°, 13.0±0.2°, 16.5±0.2° and 20.3±0.2°. Further preferable is 8.3±0.2°, 10.1±0.2°, 13.0±0.2° and 20.3±0.2°.

Example 13

Synthesis of a Crystalline Solid of Hydrate of 2 Mole Equivalents of p-toluenesulfonic Acid Salt of the Compound (IA)

The type I crystal D (25.9 g) obtained by the method described in Example 6-1 was dissolved in a mixture of acetonitrile (40 mL) and water (40 mL). Water (259 mL) was further added, and p-toluenesulfonic acid monohydrate (103.5 g) was added. The solution was cooled to 5° C. and left to stand for 65 hours, the precipitated crystalline solid was filtered. The crystal was washed with water cooled to 5° C. (80 mL) to yield a crystalline solid (15.0 g).

The contents of p-toluenesulfonic acid and sulfuric acid of the obtained crystalline solid was quantified by the method described in the above Example 6-1.

(Result)

p-Toluenesulfonic acid: 31.3±0.2% (on an anhydrous basis)
Sulfuric acid: 0.0±0.1% (on an anhydrous basis)
Elemental analysis: (calculated as $C_{30}H_{34}N_7ClO_{10}S_2$ $2.0C_7H_8O_3S$ $10.5H_2O$)
Calculated: C, 41.10(%), H, 5.57(%), N, 7.63(%), Cl, 2.76(%), S, 9.97(%), $H_2O$, 14.71(%)
Measured: C, 40.82(%), H, 5.43(%), N, 7.75(%), Cl, 2.83 (%), S, 10.05(%), $H_2O$ (KF method) 14.91(%).

The result of the X-ray powder diffraction measured by Measurement condition 2 is shown in FIG. 18 and Table 19. It should be noted that the aluminium plate is used as a sample folder. The peak whose 2-theta (2θ) value is around 38° is the peak of aluminium.

TABLE 19

| Diffraction angle 2θ (°) |
| --- |
| 5.3 |
| 8.0 |
| 8.8 |
| 10.5 |
| 10.9 |
| 13.1 |
| 17.4 |
| 19.0 |
| 19.7 |
| 20.3 |
| 21.3 |
| 24.4 |
| 25.1 |
| 26.3 |
| 27.6 |
| 29.0 |

The diffraction angles (2θ) showing characteristic diffraction peaks are 5.3±0.2°, 8.0±0.2°, 8.8±0.2°, 10.5±0.2°, 10.9±0.2°, 13.1±0.2°, 17.4±0.2°, 19.0±0.2°, 19.7±0.2°, 20.3±0.2°, 21.3±0.2°, 24.4±0.2° and 26.3±0.2°. Preferable is 5.3±0.2°, 8.0±0.2°, 8.8±0.2°, 13.1±0.2°, 17.4±0.2°, 19.0±0.2°, 20.3±0.2° and 26.3±0.2°. Further preferable is 5.3±0.2°, 8.0±0.2°, 13.0±0.2°, 19.0±0.2° and 20.3±0.2°.

Test Example 1

The Solid Stability Test of Crystalline Solid

The type I crystal D about 1 g was put in a polyethylene bag and tightened with a convex. This bag was further put in a polyethylene bag and tightened with a convex in the same way. The above sample of the same storage conditions was put together in a metal can as a stability evaluation sample. The storage conditions, storage period and test items are as follows.

There was no change in the appearance in the type I crystal D under the following storage condition and storage period, and an increase of content of its related substances was also not observed, and it was confirmed to be a very stable.

(Storage Conditions)

Temperature: −20±5° C. or 5±5° C.

Light shielding

Package form: double polyethylene bag, convex, metal can

Storage period: 0, 3, 6, 9, 12 months (Measurement)

Using the type I crystal D stored at the above storage conditions and storage period, after viewing the change in appearance, the contents of the compound (IA) and the related substances were measured by the following method.

Step 1: Preparation of a Sample Solution

About 40 mg of the sample was weighed precisely, and dissolved in a sample dilution solvent to be exactly 25 mL.

5 mmol/L phosphate buffer/liquid chromatography acetonitrile mixture (9:1) was used as the above sample dilution solvent was used. Herein, water: 0.05 mol/L sodium dihydrogen phosphate test solution: 0.05 mol/L disodium hydrogen phosphate reagent mixture=18:1:1 (pH is about 7.1) was used as a phosphate buffer.

Step 2: HPLC Measurement of Related Substances

The above sample solution was measured by liquid chromatography under the following test condition to measure peak areas of the compound (IA) and its related substances by the automatic integration method.

(HPLC Condition)
Column: YMC-UltraHT Pro C18, φ2.0×100 mm, 2 μm, YMC
Column temperature: 35° C.
UV detection wavelength: 261 nm
Mobile phase: [A] 0.1% trifluoroacetic acid solution, [B] acetonitrile for liquid chromatography
Gradient Program

| Time after addition (minute) | Mobile phase A (vol %) | Mobile phase B (vol %) |
|---|---|---|
| 0~0.6 | 95→90 | 5→10 |
| 0.6~3.3 | 90→88 | 10→12 |
| 3.3~4.5 | 88 | 12 |
| 4.5~7.0 | 88→87 | 12→13 |
| 7.0~12.4 | 87→65 | 13→35 |
| 12.4~12.5 | 65→95 | 35→5 |
| 12.5~15.0 | 95 | 5 |

Flow rate: 0.5 mL per minute (a retention time of the compound (IA) about 5 minutes)

The amount of related substances in the sample was determined by using the following formula.

$$\text{An amount of each related substance (\%)} = \frac{A_i}{A_T} \times 100$$

$$\text{Total amount of related substances (\%)} = \frac{\sum A_i}{A_T} \times 100$$

$A_i$: peak area of each related substance except the p-toluenesulfonic acid
$\Sigma A_i$: Total of peak area of each related substances except the p-toluenesulfonic acid
$A_T$: Total of peak area except system peak and p-toluenesulfonic acid Step 3: HPLC Measurement of the Compound (IA)
(Preparation of a Standard Solution)

About 40 mg of a standard preparation of the type I crystal D of the compound (IA) was weighed precisely, and dissolved in a sample dilution solvent to be exactly 25 mL.

(Preparation of a Sample Solution)

About 40 mg of a sample equilibrated humidity was weighed precisely, and was dissolved in a sample dilution solvent to be exactly 25 mL.

5 mmol/L phosphate buffer/liquid chromatography acetonitrile mixture (9:1) was used as the above sample dilution solvent. Herein, water: 0.05 mol/L sodium dihydrogen phosphate test solution: 0.05 mol/L disodium hydrogen phosphate reagent mixture=18:1:1 (pH is about 7.1) was used as a phosphate buffer.

The above standard solution and sample solution was measured by liquid chromatography under the following test condition to determine a peak area of the compound (IA) by an automatic integration method.

(HPLC Condition)
Column: YMC-UltraHT Pro C18, φ2.0×100 mm, 2 μm, YMC
Column temperature: 35° C.
UV detection wavelength: 261 nm
Flow rate: 0.5 mL per minute (a retention time of the compound (IA) about 5 minutes)
mobile phase: [A] 0.1% trifluoroacetic acid solution, [B] acetonitrile for liquid chromatography
Gradient Program

| Time after addition (minute) | Mobile phase A (vol %) | Mobile phase B (vol %) |
|---|---|---|
| 0~0.6 | 95→90 | 5→10 |
| 0.6~3.3 | 90→88 | 10→12 |
| 3.3~4.5 | 88 | 12 |
| 4.5~7.0 | 88→87 | 12→13 |
| 7.0~12.4 | 87→65 | 13→35 |
| 12.4~12.5 | 65→95 | 35→5 |
| 12.5~15.0 | 95 | 5 |

The content of related substances in the sample was determined using the following formula.

The content of the compound (IA)
($C_{30}H_{34}ClN_7O_{10}S_2$) on an anhydrous basis
(%)=$M_S/M_T \times C/1000 \times 100/(100-W_T) \times A_T/A_S \times 100$ $M_S$: weighed amount of the standard preparation of the type I crystal of the compound (IA) (mg)
$M_T$: weighed amount of the sample (mg)
C: a content of the standard sample of the type I crystal of the compound (IA) (μg/mg)
$W_T$: water equilibrated humidity of sample (%)
$A_S$: a peak area of the compound (IA) obtained from the standard solution
$A_T$: a peak area of the compound (IA) obtained from the sample solution Formulation Sample 1

The type I crystal D (123.1 g: 82.5 g as the compound (IA)) was suspended in 1155 g of water for injection, 8 wt % of sodium hydrate aqueous solution was added to the suspension until reached pH6 (added amount 159.2 g), and water for injection for weight adjustment was added to the solution to prepare a solution of 50 mg/g as the compound (IA). In this case, it took 2 hours for neutralizing dissolution. This solution was sterile filtered through a PVDF membrane with 0.2 μm of hole diameter. The obtained filtrate was put into a glass vial, followed by lyophilizing. As the condition of lyophilization, the primary during was conducted by 1) cooling at 5° C., 2) cooling for 1 hour at −5° C., 3) freezing for 4 hours at −40° C., 4) −° C. for 123 hours at 10 Pa vacuum pressure, and the second drying was conducted at 5) 60° C. for 6 hours at 10 Pa vacuum pressure to produce a lyophilized product.

The invention claimed is:
1. An acid addition salt or a sodium salt of a compound represented by formula (IA):

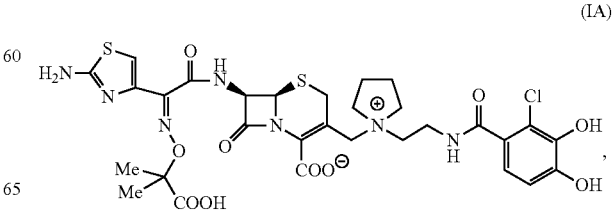

(IA)

or a hydrate of the acid addition salt or of the sodium salt, provided that the acid is
1) an acid having a substituted or unsubstituted benzenesulfonic acid group, which is at least one acid selected from the group consisting of p-toluenesulfonic acid, benzenesulfonic acid, trifluoromethyl benzenesulfonic acid, chlorobenzenesulfonic acid, and methoxybenzenesulfonic acid, or
2) a mixed acid comprising: the acid having a substituted or unsubstituted benzenesulfonic acid group; and at least one inorganic acid.

2. The acid addition salt or the hydrate thereof according to claim 1.

3. The acid addition salt or the hydrate thereof according to claim 1,
wherein the acid addition salt is formed from acid selected from the group consisting of (i) p-toluenesulfonic acid, (ii) benzenesulfonic acid, and (iii) a combination of p-toluenesulfonic acid or benzenesulfonic acid, and an inorganic acid selected from the group consisting of sulfuric acid, hydrochloric acid, and hydrobromic acid.

4. The acid addition salt or the hydrate thereof according to claim 1,
wherein the salt is (i) p-toluenesulfonic acid salt, or (ii) a salt formed from a combination of p-toluenesulfonic acid and sulfuric acid.

5. The acid addition salt or the hydrate thereof according to claim 4, comprising about 1.0 to 2.0 mole equivalents of p-toluenesulfonic acid relative to the compound of the formula (IA).

6. The acid addition salt or the hydrate thereof according to claim 4, comprising:
about 1.0 to 1.8 mole equivalents of p-toluenesulfonic acid; and
about 0.1 to 0.5 mole equivalents of sulfuric acid, relative to the compound of the formula (IA).

7. The acid addition salt or the hydrate thereof according to claim 1, which is a crystalline solid.

8. The acid addition salt or the hydrate thereof according to claim 4, which is a crystalline solid.

9. The acid addition salt or the hydrate thereof according to claim 8, which is a single phase crystal or a mixed crystal.

10. The hydrate according to claim 4, wherein a content of water in the hydrate is in a range of about 12 to 17%.

11. The acid addition salt or the hydrate thereof according to claim 8, wherein the crystalline solid is a mixed crystal comprising:
a single phase crystal of 2 mole equivalents of p-toluenesulfonic acid salt or its hydrate, relative to the compound of the formula (IA); and
a single phase crystal comprising:
1 mole equivalent of p-toluenesulfonic acid salt; and
0.5 mole equivalents of sulfuric acid salt or its hydrate, relative to the compound of the formula (IA).

12. The crystalline solid of the hydrate according to claim 7, which is a mixed acid addition salt formed from 1.3 mole equivalents of p-toluenesulfonic acid and 0.35 mole equivalents of sulfuric acid, relative to the compound of the formula (IA).

13. The crystalline solid of the hydrate thereof according to claim 7, comprising:
about 20.2 to 23.2% of p-toluenesulfonic acid on an anhydrous basis; and
about 3.5 to 5.0% sulfuric acid on an anhydrous basis.

14. The crystalline solid of the acid addition salt or the hydrate thereof according to claim 8,
wherein the crystalline solid has at least three peaks of diffraction angles (2θ) selected from the group consisting of 8.2°±0.2°, 10.1°±0.2°, 13.0°±0.2°, and 20.3°±0.2°, in an X-ray powder diffraction spectrum.

15. The crystalline solid according to claim 8,
wherein the crystalline solid has at least three peaks of diffraction angles (2θ) selected from the group consisting of 8.2°±0.2°, 8.9°±0.2°, 10.1°±0.2°, 11.4°±0.2°, 13.0°±0.2°, 19.9°±0.2°, 20.3°±0.2°, 21.5°±0.2°, and 26.2°±0.2°, in an X-ray powder diffraction spectrum.

16. The crystalline solid according to claim 8,
wherein the crystalline solid has at least three peaks of diffraction angles (2θ) selected from the group consisting of 8.2°±0.2°, 8.9°±0.2°, 10.1°±0.2°, 13.0°±0.2°, 16.5°±0.2°, 17.1°±0.2°, 17.9°±0.2°, 19.0°±0.2°, 20.3°±0.2°, and 26.2°±0.2°, in an X-ray powder diffraction spectrum.

17. A pharmaceutical composition comprising the acid addition salt or the hydrate thereof according to claim 1, or a crystalline solid thereof.

18. A process for preparing the crystalline solid of the acid addition salt or the hydrate thereof according to claim 8, comprising adding p-toluenesulfonic acid and sulfuric acid to a solution that comprises the compound of the formula (IA).

19. The process for preparing the crystalline solid according to claim 18, wherein about 2.2 to 2.5 wt % of p-toluenesulfonic acid monohydrate and about 5 to 6 wt % of sulfuric acid are added to a column eluate that comprises the compound of the formula (IA).

20. The sodium salt or the hydrate thereof according to claim 1.

21. The sodium salt or the hydrate thereof according to claim 20, which is amorphous.

22. A pharmaceutical composition comprising the sodium salt or the hydrate thereof according to claim 20.

23. The pharmaceutical composition according to claim 22, which is a lyophilized formulation.

24. A method for preparing a lyophilized formulation comprising the sodium salt of the compound of the formula (IA) or the hydrate thereof, comprising:
using a composition comprising the acid addition salt or the hydrate thereof according to claim 1, or a crystalline solid thereof.

25. A method for preparing a lyophilized formulation comprising the sodium salt of the compound of the formula (IA) or the hydrate thereof, comprising:
lyophilizing a solution comprising:
the acid addition salt or the hydrate thereof according to claim 1, or a crystalline solid thereof; and
sodium hydrate.

26. The method for preparing the lyophilized formulation according to claim 24, wherein the acid addition salt is formed from (i) p-toluenesulfonic acid, or (ii) a combination of p-toluenesulfonic acid and sulfuric acid.

27. A pharmaceutical composition comprising:
a compound represented by formula (IA);

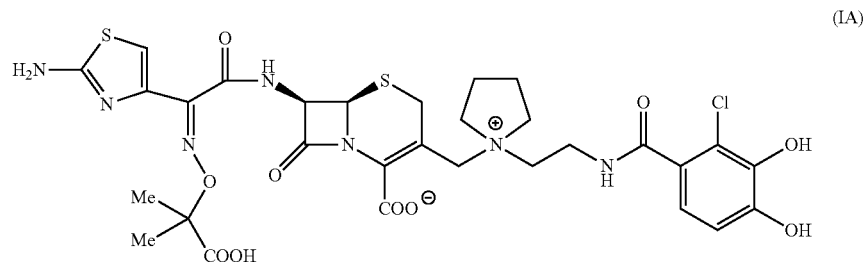

or
a pharmaceutically acceptable salt thereof, or a hydrate of the compound or of the pharmaceutically acceptable salt thereof; and
sodium p-toluenesulfonate, or sodium sulfate, or a combination thereof.

28. The pharmaceutical composition according to claim 27, comprising:
a sodium salt of the compound of the formula (IA) or the hydrate thereof; and
sodium p-toluenesulfonate, or sodium sulfate, or a combination thereof.

* * * * *

UNITED STATES PATENT AND TRADEMARK OFFICE
CERTIFICATE OF CORRECTION

PATENT NO. : 10,004,750 B2
APPLICATION NO. : 15/508270
DATED : June 26, 2018
INVENTOR(S) : Matsubara It is certified that error appears in the above-identified patent and that said Letters Patent is hereby corrected as shown below:

On the Title Page

Item "*", Column 1, in "Notice", Line 3, after "0 days." delete the repeated "days.".

In the Specification

Column 5, Line 32, delete "salvates" and insert -- solvates --.

Column 6, Line 20, delete "bensenesulfonic" and insert -- benzenesulfonic --.

Column 7, in "Chemical formula 5", Line 1, delete "$H_3C$" and insert -- $H_2N$ --.

Column 7, in "Chemical formula 6", Line 1, delete "$H_3C$" and insert -- $H_2N$ --.

Column 7, Line 59, delete "phydicochemical" and insert -- physicochemical --.

Column 9, Line 56, delete "(non-solvete)" and insert -- (non-solvate) --.

Column 10, Line 26, delete "salvate" and insert -- solvate --.

Column 10, Line 47, delete "acid-sufuric" and insert -- acid-sulfuric --.

Column 12, Line 44, delete "26.2±0.2." and insert -- 26.2±0.2°. --.

Column 13, Line 16, delete "angel" and insert -- angle --.

Column 16, Line 34, delete "FIG." and insert -- FIGS. --.

Column 16, Line 52, delete "methods" and insert -- method --.

Signed and Sealed this
Twenty-first Day of May, 2019

Andrei Iancu
*Director of the United States Patent and Trademark Office*

CERTIFICATE OF CORRECTION (continued)
U.S. Pat. No. 10,004,750 B2

Column 17, Line 59, delete "recioricals" and insert -- reciprocals --.

Column 18, Line 35, delete "Thermogravimeric" and insert -- Thermogravimetric --.

Column 19, Line 55, delete "or or" and insert -- or --.

Column 20, Line 57, delete "mousewashs," and insert -- mouthwashes, --.

Column 21, Line 24, delete "transmucosa," and insert -- transmucosal, --.

Column 21, Line 27, delete "intranosal," and insert -- intranasal, --.

Column 22, Line 5, delete "preservatibe," and insert -- preservative, --, therefor.

Column 22, Line 6, delete "ohenol," and insert -- phenol, --.

Column 24, Line 10, after "300°" insert -- C. --.

Column 25, Line 29, delete "p-toluenesolufonic" and insert -- p-toluenesulfonic --.

Column 25, Line 50, delete "$2.00_7$" and insert -- $2.0C_7$ --.

Column 26, Line 8, delete "$2.00_7$" and insert -- $2.0C_7$ --.

Column 33, Line 12, delete "$1.30O_7$" and insert -- $1.30C_7$ --.

Column 33, Line 42, after "are" delete ",".

Column 35, Line 48, delete "angels" and insert -- angles --.

Column 36, Line 19, delete "angels" and insert -- angles --.

Column 40, Line 37, delete "angels" and insert -- angles --.

Column 46, Line 46, delete "-20±5° C. or 5±5° C." and insert -- -20° C.±5° C. or 5° C.±5° C. --.